(12) United States Patent
Chang et al.

(10) Patent No.: US 9,162,993 B2
(45) Date of Patent: Oct. 20, 2015

(54) PREPARATION AND PHARMACEUTICALS OF BIPHENYL BENZAMIDE-DERIVED DERIVATIVES

(71) Applicant: NATIONAL DEFENSE MEDICAL CENTER, Taipei (TW)

(72) Inventors: Deh-Ming Chang, Taipei (TW); Hsu-Shan Huang, Taipei (TW); Chia-Chung Lee, Taipei (TW); Chun-Liang Chen, Taipei (TW)

(73) Assignee: National Defense Medical Center, Taipei (TW)

( * ) Notice: Subject to any disclaimer, the term of this patent is extended or adjusted under 35 U.S.C. 154(b) by 0 days.

(21) Appl. No.: 14/608,905

(22) Filed: Jan. 29, 2015

(65) Prior Publication Data

US 2015/0191438 A1    Jul. 9, 2015

Related U.S. Application Data

(62) Division of application No. 13/571,158, filed on Aug. 9, 2012, now Pat. No. 8,975,255.

(30) Foreign Application Priority Data

Apr. 18, 2012  (TW) .............................. 101113752 A

(51) Int. Cl.

| | | |
|---|---|---|
| C07C 231/02 | (2006.01) | |
| C07C 235/64 | (2006.01) | |
| C07C 235/66 | (2006.01) | |
| C07C 255/60 | (2006.01) | |
| C07D 265/18 | (2006.01) | |
| C07D 265/26 | (2006.01) | |
| C07C 47/55 | (2006.01) | |
| C07C 231/10 | (2006.01) | |

(52) U.S. Cl.
CPC .............. *C07D 265/18* (2013.01); *C07C 47/55* (2013.01); *C07C 231/10* (2013.01); *C07C 235/64* (2013.01); *C07C 255/60* (2013.01); *C07D 265/26* (2013.01)

(58) Field of Classification Search
CPC .. C07C 231/02; C07C 235/64; C07C 235/66; C07C 255/60
USPC ............ 564/174, 176, 179; 514/522; 558/415
See application file for complete search history.

(56) References Cited

U.S. PATENT DOCUMENTS

2013/0281412 A1    10/2013  Chang et al.

FOREIGN PATENT DOCUMENTS

WO    WO 2006077901 A1 *  7/2006

* cited by examiner

*Primary Examiner* — Kahsay Habte
(74) *Attorney, Agent, or Firm* — Muncy, Geissler, Olds & Lowe, P.C.

(57) ABSTRACT

The present invention provides a biphenyl benzamide-derived derivatives, which structure is selected from formula I or formula II

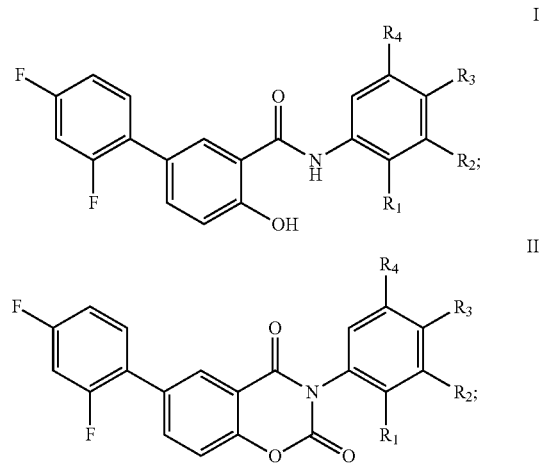

and the synthesis and the application thereof.

9 Claims, 11 Drawing Sheets

(−) RANKL (100ng/mL) + DMSO (0.1 %)

(+) RANKL (100ng/mL) + DMSO (0.1 %)

(+) RANKL (100ng/mL) + Compd. LCC-04 (5 μM)

(+) RANKL (100ng/mL) + Compd. LCC-16 (5 μM)

(-) RANKL (100ng/mL) + DMSO (0.1 %)

(+) RANKL (100ng/mL) + DMSO (0.1 %)

(+) RANKL (100ng/mL) + Compd. LCC-04 (5 μM)

(+) RANKL (100ng/mL) + Compd. LCC-16 (5 μM)

PREPARATION AND PHARMACEUTICALS OF BIPHENYL BENZAMIDE-DERIVED DERIVATIVES

CROSS-REFERENCE TO RELATED APPLICATIONS

This application is a Divisional of co-pending application Ser. No. 13/571,158, filed on Aug. 9, 2012, for which priority is claimed under 35 U.S.C. §120; and this application claims priority of Application No. 101113752 filed in Taiwan on Apr. 18, 2012 under 35 U.S.C. §119; the entire contents of all of which are hereby incorporated by reference.

FIELD OF THE INVENTION

The present invention is related to a pharmaceutical composition of biphenyl benzamide-derived derivatives, the synthesis and the application thereof, especially related to the application of treating inflammatory reaction, osteoporosis, osteoarthritis and cancer.

BACKGROUND OF THE INVENTION

In the bone regeneration process, once the balance of the bone remodeling is broken, the bone resorption of the osteoclasts is dominated over bone formation of the osteoblasts, the bone remodeling would be imbalanced. As a result, the osteocytes would decrease, osteopenia or bone mineral density decrease to induce lots of bone disease, such as osteoporosis, periodontitis or osteoarthritis.

The osteoclasts origins from hematopoietic precursor cells. Further, the Macrophage-Colony Stimulating Factor (M-CSF) secreted by osteoblast and Receptor Activator of Nuclear factor Kappa B Ligand (RANK. L) would combine with the c-Fms and RANK on the cell membrane of the osteoclast precursor cells, and induce the secretion of tartrate-resistant acid phosphatase (TRAP), integrin b3 expression, and actin ring formation, etc. These changes of protein activity and cell morphology would enhance the osteoclasts motility and help the osteoclasts adhere on the bone surface. On the other hand, the expression of cathepsin K matrix metalloproteinase-9 (MMP-9), dendritic cell-specific transmembrane protein (DC-STAMP), ATPase, H+ transporting lysosomal V0 subunit D2(ATP6V0D2) would induce the osteoclast precursor cells differentiate into a hung matured (diameter is 20-100 mm) multinucleated cells (MNCs) (containing 4-20 nucleus), which also have the bone resorption function.

The osteoblasts would secret M-CSF and RANKL, which induce the osteocytes growth and differentiation, and would also secret the osteoprotegerin (OPG). OPG would associate with RANKL to prevent the association of RANKL and RANK, so as to prevent the formation of osteoclasts and inhibit the formation of osteoclasts, to decrease the bone resorption; besides, OPG would involve in the osteoclast apoptosis.

SUMMARY OF THE INVENTION

For the purpose, the present invention provides a series of pharmaceutical compositions of biphenyl benzamide-derived derivatives, wherein the pharmaceutical compositions can be used for treating inflammatory reaction, cancer and preventing osteoporosis and osteoarthritis effectively.

The present invention provides a biphenyl benzamide-derived derivatives, which structure is selected from formula I or formula II:

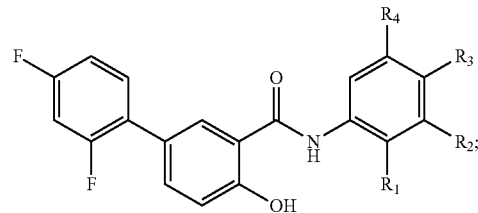

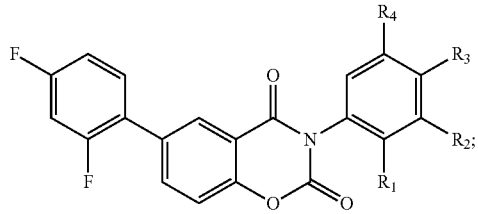

The present invention provides a pharmaceutical composition of biphenyl benzamide-derived derivatives, which comprises:

(a) a structure is selected from formula I or formula II:

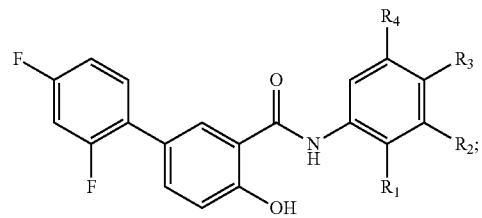

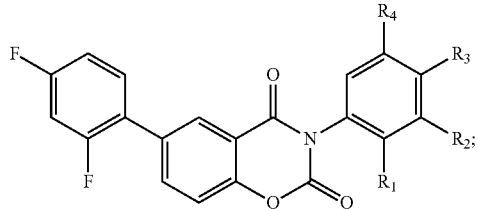

(b) a pharmaceutical acceptable salt and carrier of the biphenyl benzamide-derived derivatives.

Preferably, the $R_1$, $R_2$, $R_3$ and $R_4$ of the formula I or formula II can be selected from the group of H, halogen, $CF_3$, CN, CH and $OCH_3$.

Preferably, the pharmaceutical acceptable carrier is excipient, diluents, thickeners, filler, binder, disintegrants, lubricant, oil or non-oil base, surfactant, suspending agent, gelling agent, adjuvant, anti-corrosive agent, anti-oxidant, stabilizer, coloring agent or flavor.

Preferably, the salt is physiological acceptable salt of inorganic acid, inorganic base, organic acid or organic base.

Preferably, the composition is powder, granule, liquid, gel or cream.

Preferably, the composition is administrated through oral, transdermal, injection, or inhalational manner.

The present invention also provides a method for synthesis of the compound of formula I, which is synthesized by difunisal:

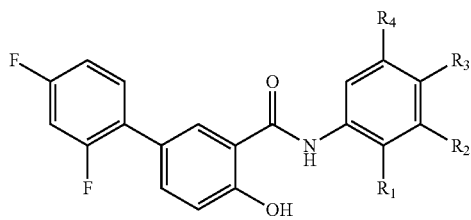

The present invention also provides a method for synthesis of the compound of formula II, which is synthesized by compound of formula I:

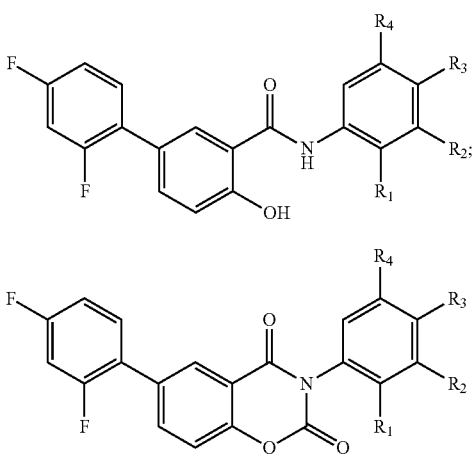

Preferably, the compound of formula I is synthesized by amine, tetrahydrofuran and an intermediate compound which is synthesized by difunisal, tetrahydrofuran and thionyl chloride.

Preferably, the compound of formula II is synthesized by compound of formula I, tetrahydrofuran/pyridine and methyl chloroformate.

Preferably, the pharmaceutical composition can be used as anti-inflammatory agent, osteoporosis therapeutics or osteoarthritis therapeutics.

DETAILED DESCRIPTION OF THE INVENTION

Figure 1A:
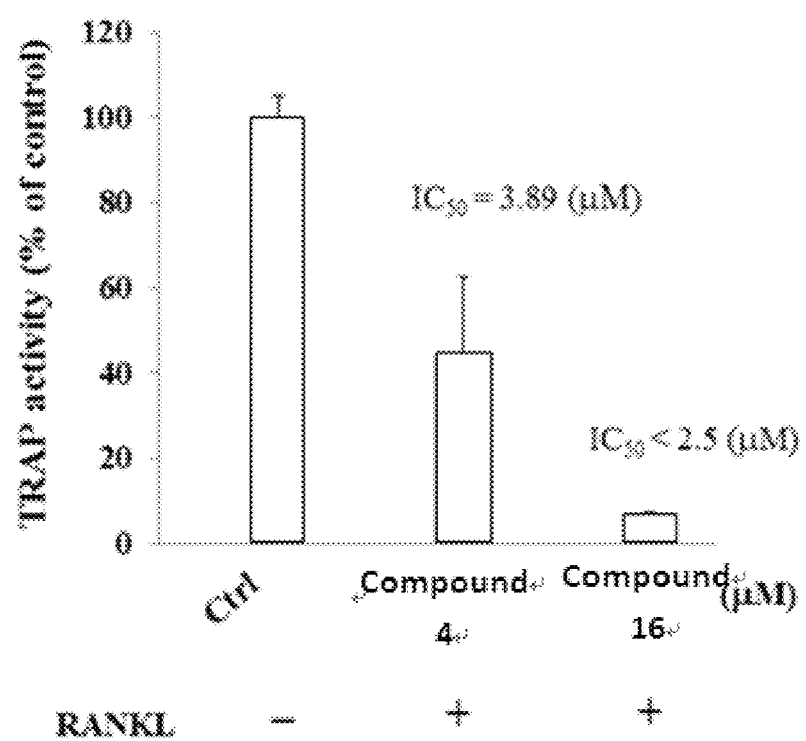
FIG. 1A shows the effects of different concentration of compound 4 and compound 16 on the osteoclast proliferation.

The present invention provides a series of pharmaceutical compositions of biphenyl benzamide-derived derivatives, which can be used to inhibit the osteoclast growth so as to decrease the bone resorption and prevent the osteoporosis.

The structure of a biphenyl benzamide-derived derivative is selected from formula I or formula II:

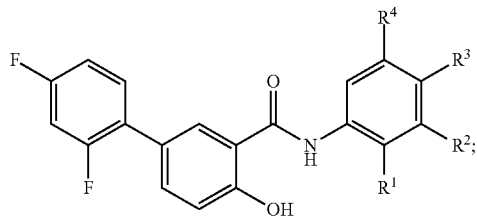

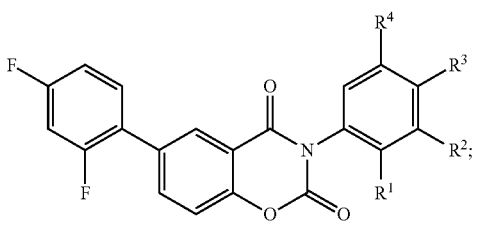

The pharmaceutical composition of the present invention comprises, but not limited to, (a) a structure is selected from formula I or formula II:

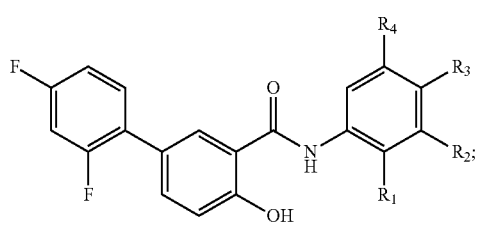

-continued

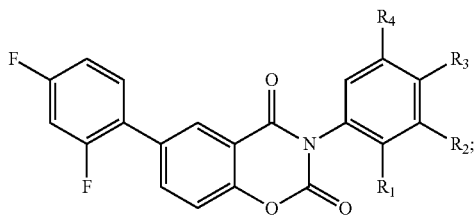

(b) a pharmaceutical acceptable salt and carrier of the biphenyl benzamide-derived derivatives.

In the best embodiment, the $R_1$, $R_2$, $R_3$ and $R_4$ of the formula I or formula II can be selected from the group consisting of H, halogen, $CF_3$, CN, CH and $OCH_3$.

The present invention also provides a method for synthesis of the compound of formula I, which is synthesized by difunisal:

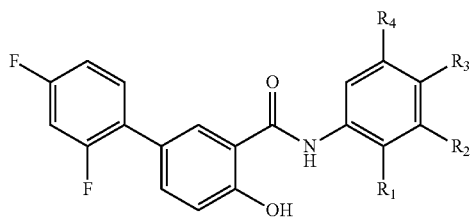

The present invention also provides a method for synthesis of the compound of formula II, which is synthesized by compound of formula I:

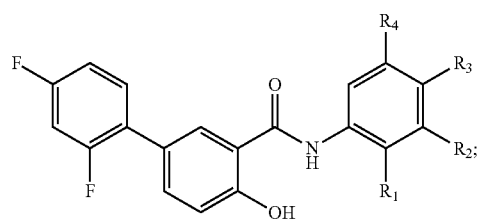

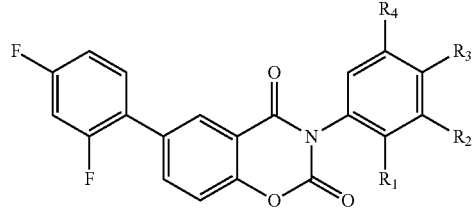

In the best embodiment, the compound of formula I is synthesized by amine, tetrahydrofuran and an intermediate compound which is synthesized by difunisal, tetrahydrofuran and thionyl chloride.

In the best embodiment, the compound of formula II is synthesized by compound of formula I, tetrahydrofuran/pyridine and methyl chloroformate.

The present invention provides a method for treating inflammation, osteoporosis, or osteoarthritis by said pharmaceutical composition of the biphenyl benzamide-derived derivatives.

In the best embodiment, the pharmaceutical acceptable carrier is excipient, diluents, thickeners, filler, binder, disintegrants, lubricant, oil or non-oil base, surfactant, suspending agent, gelling agent, adjuvant, anti-corrosive agent, anti-oxidant, stabilizer, coloring agent or flavor.

In the best embodiment, the excipient can be, but not limited to, diluents, filler, binder, disintegrants, etc. Wherein the excipient can be, but not limited to, microcrystalline cellulose, polyvinylpyrrolidone (PVP), modified starches, sodium starch glycolate, gelatinized starches, polyethylene glycol (PEG), polyvinyl alcohol, hydroxypropyl cellulose, methylcellulose, hydroxymethyl cellulose, hydroxypropyl methylcellulose.

In the best embodiment, the salt can be physiological acceptable salt of inorganic acid, inorganic base, organic acid or organic base. Besides, the pharmaceutical composition is powder, granule, liquid, gel or cream. In addition, the pharmaceutical composition is administrated through oral, transdermal, injection, or inhalational manner.

As mentioned above, the various substitutes would be listed in Table 1, and the synthesis method of these biphenyl benzamide-derived derivatives would be further disclosed in the embodiments.

The embodiments of the present invention are listed in Table 2, this table shows the structure of the biphenyl benzamide-derived derivatives of the present invention.

TABLE 1

| the $R_1$ to $R_4$ of the compounds of the present invention | | | | |
|---|---|---|---|---|
| Compounds | $R_1$ | $R_2$ | $R_3$ | $R_4$ |
| compound 1 and compound 13 | F | H | Cl | H |
| compound 2 and compound 14 | F | H | F | H |
| compound 3 and compound 15 | H | F | F | H |
| compound 4 and compound 16 | F | H | H | F |
| compound 5 and compound 17 | $CF_3$ | H | H | H |
| compound 6 and compound 18 | H | $CF_3$ | H | H |
| compound 7 and compound 19 | H | H | $CF_3$ | H |
| compound 8 and compound 20 | H | CH | H | H |
| compound 9 and compound 21 | H | CN | H | H |
| compound 10 and compound 22 | H | H | H | CN |
| compound 11 and compound 23 | H | $OCH_3$ | $OCH_3$ | H |
| compound 12 and compound 24 | H | $OCH_3$ | H | H |

TABLE 2

The structure of series of pharmaceutical compositions of biphenyl benzamide-derived derivatives.

| | |
|---|---|
| ![structure] | Compound 1 |

Chemical Formula: $C_{19}H_{11}ClF_3NO_2$
Exact Mass: 377.0430
Molecular Weight: 377.7443

TABLE 2-continued

The structure of series of pharmaceutical compositions of biphenyl benzamide-derived derivatives.

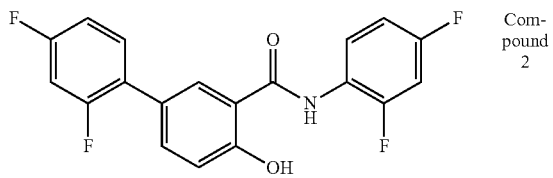

Chemical Formula: $C_{19}H_{11}F_4NO_2$
Exact Mass: 361.0726
Molecular Weight: 361.2898

Compound 2

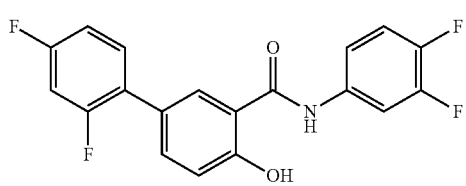

Chemical Formula: $C_{19}H_{11}F_4NO_2$
Exact Mass: 361.0726
Molecular Weight: 361.2898 compound 3

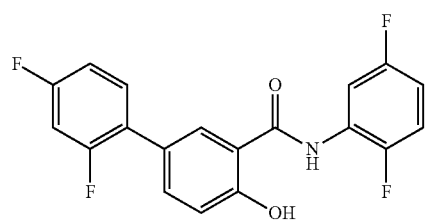

Chemical Formula: $C_{19}H_{11}F_4NO_2$
Exact Mass: 361.0726
Molecular Weight: 361.2898

Compound 4

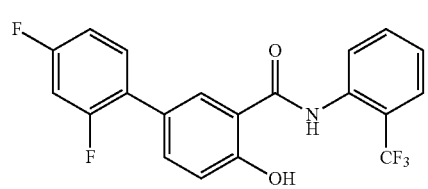

Chemical Formula: $C_{20}H_{12}F_5NO_2$
Exact Mass: 393.0788
Molecular Weight: 393.3068

Compound 5

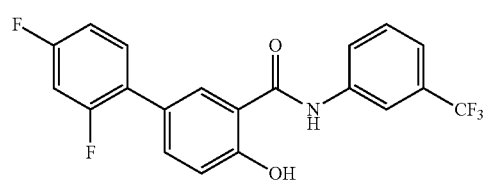

Chemical Formula: $C_{20}H_{12}F_5NO_2$
Exact Mass: 393.0788
Molecular Weight: 393.3068

Compound 6

TABLE 2-continued

The structure of series of pharmaceutical compositions of biphenyl benzamide-derived derivatives.

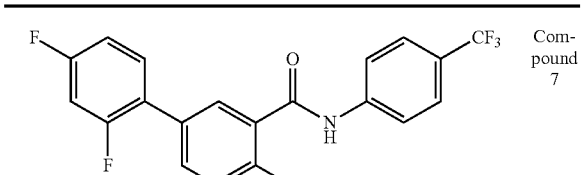

Chemical Formula: $C_{20}H_{12}F_5NO_2$
Exact Mass: 393.0788
Molecular Weight: 393.3068

Compound 7

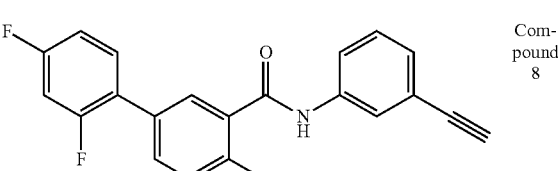

Chemical Formula: $C_{21}H_{13}F_2NO_2$
Exact Mass: 349.0914
Molecular Weight: 349.3302

Compound 8

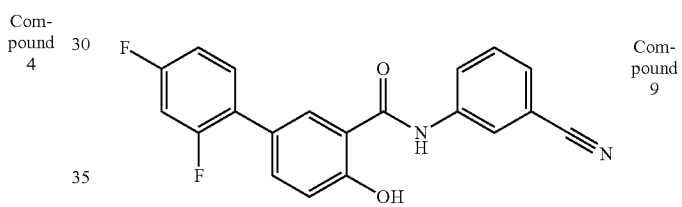

Chemical Formula: $C_{20}H_{12}F_2N_2O_2$
Exact Mass: 350.0867
Molecular Weight: 350.3183

Compound 9

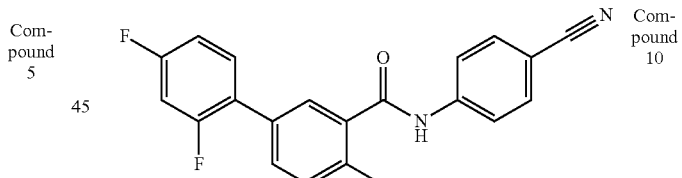

Chemical Formula: $C_{20}H_{12}F_2N_2O_2$
Exact Mass: 350.0867
Molecular Weight: 350.3183

Compound 10

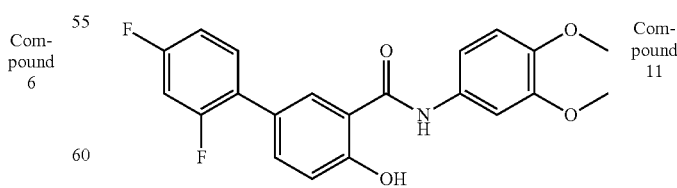

Chemical Formula: $C_{21}H_{17}F_2NO_4$
Exact Mass: 385.1126
Molecular Weight: 385.3608

Compound 11

TABLE 2-continued

The structure of series of pharmaceutical compositions of biphenyl benzamide-derived derivatives.

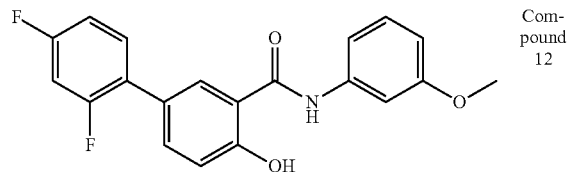

Compound 12

Chemical Formula: C$_{20}$H$_{15}$F$_2$NO$_3$
Exact Mass: 355.1020
Molecular Weight: 355.3348

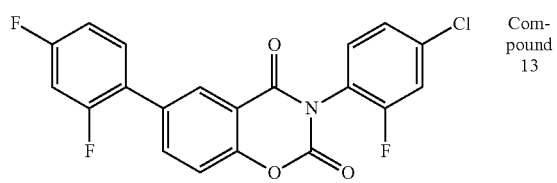

Compound 13

Chemical Formula: C$_{20}$H$_9$ClF$_3$NO$_3$
Exact Mass: 403.0223
Molecular Weight: 403.7386

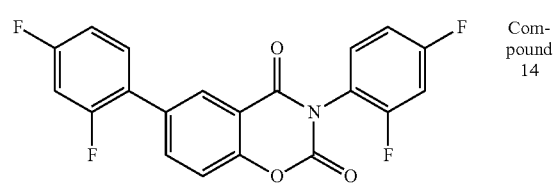

Compound 14

Chemical Formula: C$_{20}$H$_9$F$_4$NO$_3$
Exact Mass: 387.0519
Molecular Weight: 387.2840

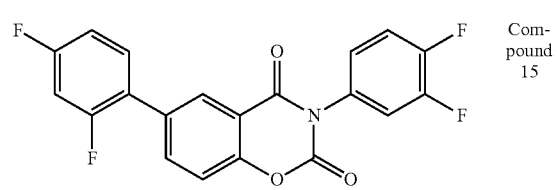

Compound 15

Chemical Formula: C$_{20}$H$_9$F$_4$NO$_3$
Exact Mass: 387.0519
Molecular Weight: 387.2840

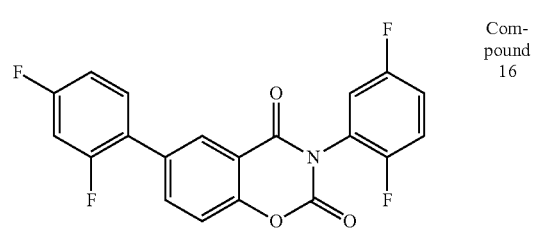

Compound 16

Chemical Formula: C$_{20}$H$_9$F$_4$NO$_3$
Exact Mass: 387.0519
Molecular Weight: 387.2840

TABLE 2-continued

The structure of series of pharmaceutical compositions of biphenyl benzamide-derived derivatives.

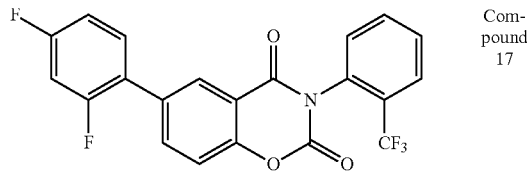

Compound 17

Chemical Formula: C$_{21}$H$_{10}$F$_5$NO$_3$
Exact Mass: 419.0581
Molecular Weight: 419.3010

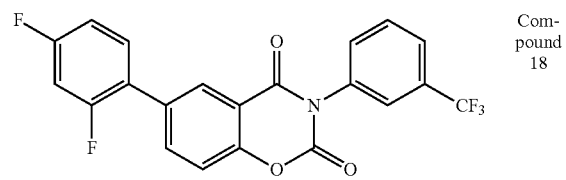

Compound 18

Chemical Formula: C$_{21}$H$_{10}$F$_5$NO$_3$
Exact Mass: 419.0581
Molecular Weight: 419.3010

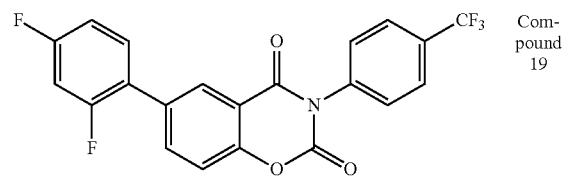

Compound 19

Chemical Formula: C$_{21}$H$_{10}$F$_5$NO$_3$
Exact Mass: 419.0581
Molecular Weight: 419.3010

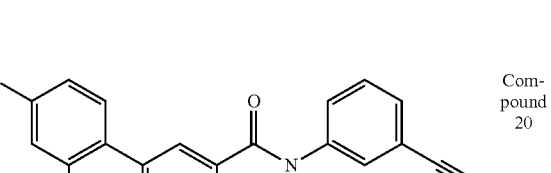

Compound 20

Chemical Formula: C$_{22}$H$_{11}$F$_2$NO$_3$
Exact Mass: 375.0707
Molecular Weight: 375.3244

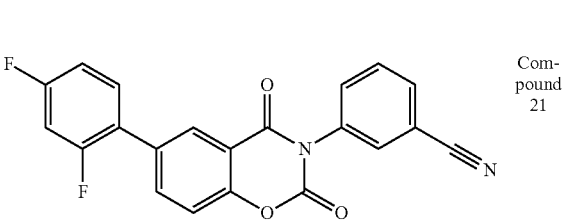

Compound 21

Chemical Formula: C$_{21}$H$_{10}$F$_5$N$_2$O$_3$
Exact Mass: 376.0659
Molecular Weight: 376.3125

TABLE 2-continued

The structure of series of pharmaceutical compositions of biphenyl benzamide-derived derivatives.

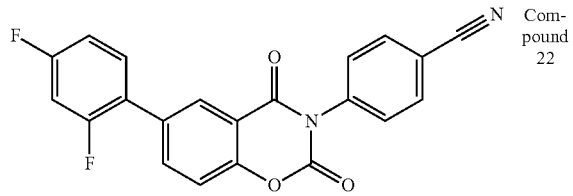

Chemical Formula: $C_{21}H_{10}F_2N_2O_3$
Exact Mass: 376.0659
Molecular Weight: 376.3125

Compound 22

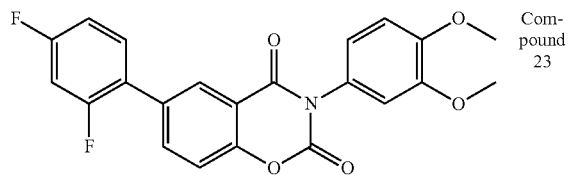

Chemical Formula: $C_{22}H_{15}F_2NO_6$
Exact Mass: 411.0918
Molecular Weight: 411.3550

Compound 23

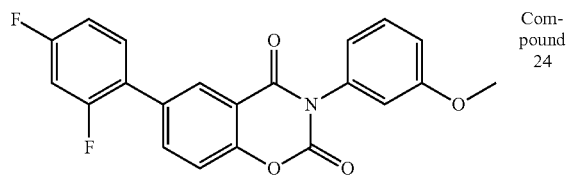

Chemical Formula: $C_{21}H_{13}F_2NO_4$
Exact Mass: 381.0813
Molecular Weight: 381.3290

Compound 24

The synthesis method and the details of the compounds 1 to 24 of the present invention is described as embodiments 1 to 24:

EXAMPLE 1

N-(4-chloro-2-fluorophenyl)-2',4'-difluoro-4-hydroxybiphenyl-3-carboxamide (compound 1)

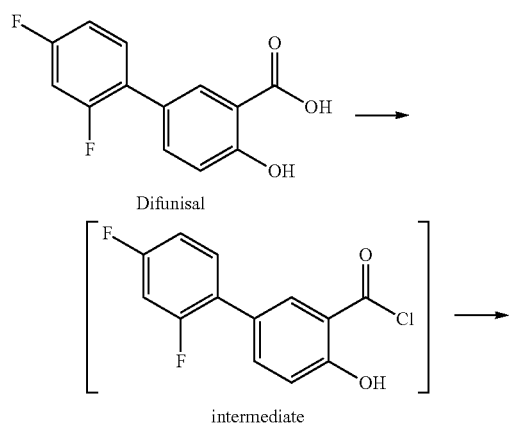

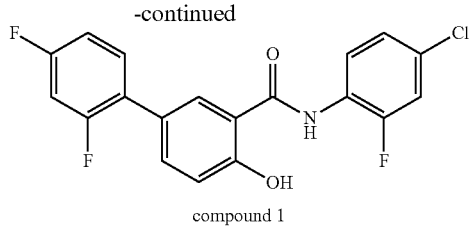

compound 1

The synthesis method of compound 1:

Thionyl chloride (1 mL, 14 mmol) was added to disfunisal (0.9 g, 4 mmol) in anhydrous tetrahydrofuran (30 mL), and the mixture was refluxed under nitrogen atmosphere for 8 h. After cooling to room temperature, the mixture was steamed to give the intermediate by Dean-Stark apparatus, which residue was used directly in the next step. Freshly prepared intermediate was directly reacted with 4-chloro-2-fluoroaniline (0.5 mL, 4 mmol) in anhydrous tetrahydrofuran (30 ml) for 14 h. After removal of tetrahydrofuran, the reaction mixture was washed with ethyl acetate/hexane and the crude product was extracted in ethyl acetate. The organic layer was collect and dried over anhydrous $Na_2SO_4$, and then the solvent was evaporated. The crude product was washed and purified by crystallization from hot ethanol to afford compound 1.

Yield: 30%. Mp: 245-246° C. (EtOH). $^1$H-NMR (300 MHz, DMSO-$d_6$): δ ppm 7.12 (d, J=6.0 Hz, 1H, Ar—$H_5$), 7.19 (td, J=9.0, 1.8 Hz, 1H, Ar—$H_{6'}$), 7.31-7.40 (m, 2H, Ar—$H_{5,6''}$), 7.55-7.64 (m, 3H, Ar—$H_{6,3',5''}$), 8.14 (t, J=1.5 Hz, 1H, Ar—$H_2$), 8.24 (t, J=8.7 Hz, 1H, Ar—$H_{3''}$), 10.77 (s, NH), 12.19 (s, 1H, OH). HRMS (EI) m/z: calcd [M]$^+$, 377.0430 ($C_{19}H_{11}ClF_3NO_2{}^+$); found, 377.33.

EXAMPLE 2

N-(2,4-difluorophenyl)-2',4'-difluoro-4-hydroxybiphenyl-3-carboxamide (compound 2)

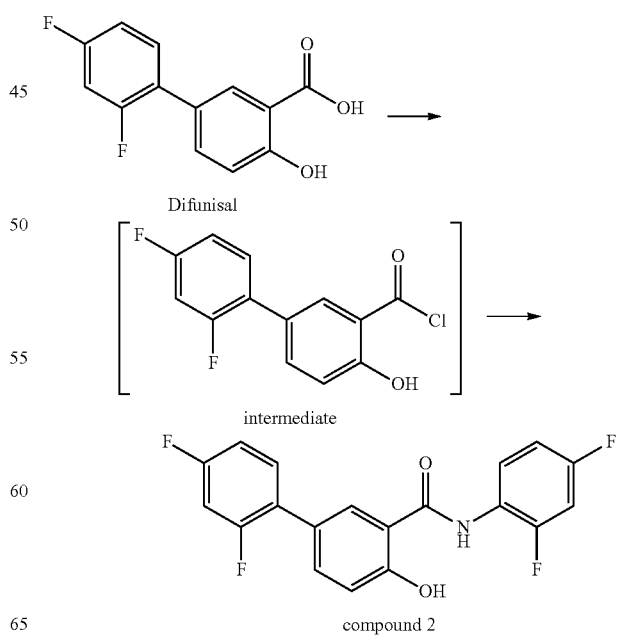

compound 2

The synthesis method of compound 2:

Thionyl chloride (1 mL, 14 mmol) was added to disfunisal (0.9 g, 4 mmol) in anhydrous tetrahydrofuran (30 mL), and the mixture was refluxed under nitrogen atmosphere for 8 h. After cooling to room temperature, the mixture was steamed to give the intermediate by Dean-Stark apparatus, which residue was used directly in the next step. Freshly prepared intermediate was directly reacted with 2,4-difluoroaniline (0.4 mL, 4 mmol) in anhydrous tetrahydrofuran (30 mL) for 14 h. After removal of tetrahydrofuran, the reaction mixture was washed with ethyl acetate/hexane and the crude product was extracted in ethyl acetate. The organic layer was collect and dried over anhydrous $Na_2SO_4$, and then the solvent was evaporated. The crude product was washed and purified by crystallization from hot ethanol to afford compound 2.

Yield: 42%. Mp: 233-234° C. (EtOH). $^1$H-NMR (300 MHz, DMSO-d$_6$): δ ppm 7.10-7.23 (m, 3H Ar—H$_{5,6',6''}$), 7.33-7.45 (m, 2H, Ar—H$_{5',5''}$), 7.55-7.64 (m, 2H, Ar—H$_{6,3'}$), 8.06-8.15 (m, 2H, Ar—H$_{2,3''}$), 10.64 (s, 1H, NH), 12.16 (s, 1H, OH). HRMS (EI) m/z: calcd [M]$^+$, 361.0726 ($C_{19}H_{11}F_4NO_2^+$); found, 361.0730.

EXAMPLE 3

N-(3,4-difluorophenyl)-2,4'-difluoro-4-hydroxy-[1,1'-biphenyl]-3-carboxamide (compound 3)

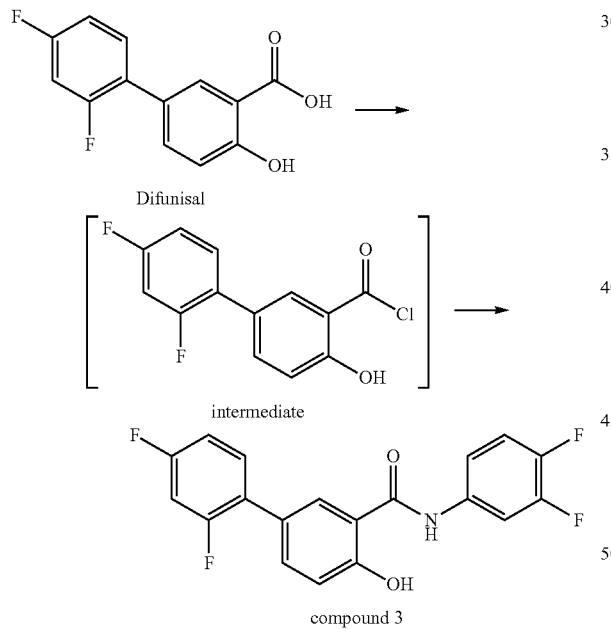

compound 3

The synthesis method of compound 3:

Thionyl chloride (1 mL, 14 mmol) was added to disfunisal (0.9 g, 4 mmol) in anhydrous tetrahydrofuran (30 mL), and the mixture was refluxed under nitrogen atmosphere for 8 h. After cooling to room temperature, the mixture was steamed to give the intermediate by Dean-Stark apparatus, which residue was used directly in the next step. Freshly prepared intermediate was directly reacted with 3,4-difluoroaniline (0.4 mL, 4 mmol) in anhydrous tetrahydrofuran (30 mL) for 14 h. After removal of tetrahydrofuran, the reaction mixture was washed with ethyl acetate/hexane and the crude product was extracted in ethyl acetate. The organic layer was collect and dried over anhydrous $Na_2SO_4$, and then the solvent was evaporated. The crude product was washed and purified by crystallization from hot ethanol to afford compound 3.

Yield: 61%. Mp: 231-232° C. (EtOH). $^1$H-NMR (300 MHz, DMSO-d$_6$): δ ppm 7.09 (d, J=8.7 Hz, 1H, Ar—H$_5$), 7.20 (td, J=8.4, 3 Hz, 1H, Ar—H$_{6'}$), 7.45-7.49 (m, 3H, Ar—H$_{3',5',6''}$), 7.56-7.64 (m, 2H, Ar—H$_{6,5''}$), 7.87-7.93 (m, 1H, Ar—H$_{6''}$), 8.01 (t, J=0.9 Hz, 1H, 10.55 (s, 1H, NH), 11.70 (s, 1H, OH). HRMS (EI) m/z: calcd [M]$^+$, 361.0726 ($C_{19}H_{11}F_4NO_2^+$); found, 361.0724.

EXAMPLE 4

N-(2,5-difluorophenyl)-2',4'-difluoro-4-hydroxy-[1,1'-biphenyl]-3-carboxamide (compound 4)

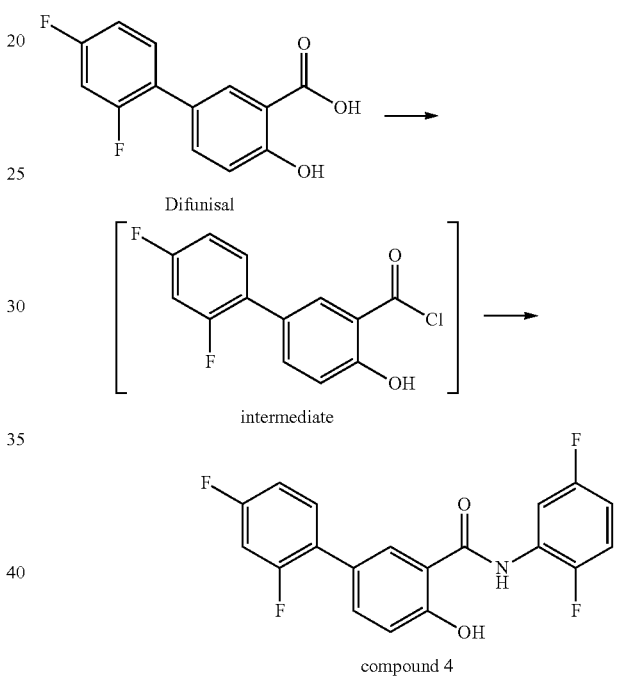

compound 4

The synthesis method of compound 4:

Thionyl chloride (1 mL, 14 mmol) was added to disfunisal (0.9 g, 4 mmol) in anhydrous tetrahydrofuran (30 mL), and the mixture was refluxed under nitrogen atmosphere for 8 h. After cooling to room temperature, the mixture was steamed to give the intermediate by Dean-Stark apparatus, which residue was used directly in the next step. Freshly prepared intermediate was directly reacted with 2,5-difluoroaniline (0.4 mL, 4 mmol) in anhydrous tetrahydrofuran (30 mL) for 14 h. After removal of tetrahydrofuran, the reaction mixture was washed with ethyl acetate/hexane and the crude product was extracted in ethyl acetate. The organic layer was collect and dried over anhydrous $Na_2SO_4$, and then the solvent was evaporated. The crude product was washed and purified by crystallization from hot ethanol to afford compound 4.

Yield: 37%. Mp: 213-214° C. (EtOH). $^1$H-NMR (300 MHz, DMSO-d$_6$): δ ppm 6.99-7.05 (m, 1H, Ar—H$_{4''}$), 7.12-7.22 (m, 2H, Ar—H$_{5,6'}$), 7.33-7.44 (m, 2H, Ar—H$_{5',3''}$), 7.55-7.65 (m, 2H, Ar—H$_{6,3'}$), 8.14-8.23 (m, 2H, Ar—H$_{2,6''}$), 10.89 (s, 1H, NH), 12.22 (s, 1H, OH). HRMS (EI) m/z: calcd [M]$^+$, 361.0726 ($C_{19}H_{11}F_4NO_2^+$); found, 361.0731.

EXAMPLE 5

2',4'-difluoro-4-hydroxy-2-(trifluoromethyl)phenyl)-[1,1'-biphenyl]-3-carboxamide (compound 5)

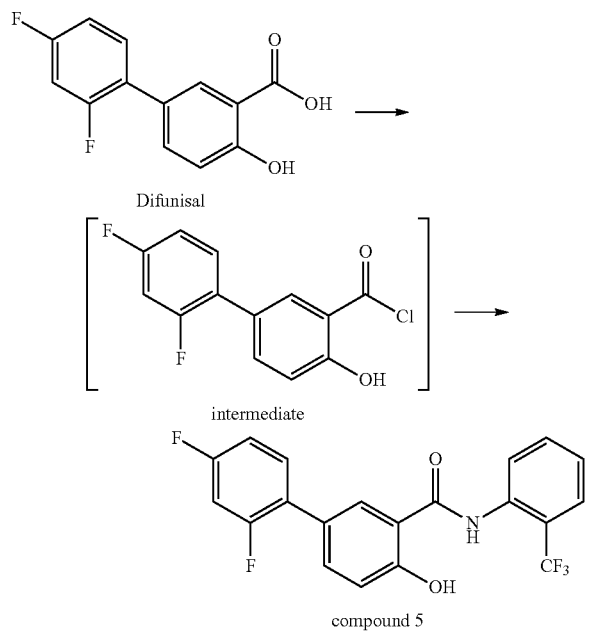

The synthesis method of compound 5:

Thionyl chloride (1 mL, 14 mmol) was added to disfunisal (0.9 g, 4 mmol) in anhydrous tetrahydrofuran (30 mL), and the mixture was refluxed under nitrogen atmosphere for 8 h. After cooling to room temperature, the mixture was steamed to give the intermediate by Dean-Stark apparatus, which residue was used directly in the next step. Freshly prepared intermediate was directly reacted with 2-(trifluoromethyl)aniline (0.5 mL, 4 mmol) in anhydrous tetrahydrofuran (30 mL) for 14 h. After removal of tetrahydrofuran, the reaction mixture was washed with ethyl acetate/hexane and the crude product was extracted in ethyl acetate. The organic layer was collect and dried over anhydrous $Na_2SO_4$, and then the solvent was evaporated. The crude product was washed and purified by crystallization from hot ethanol to afford compound 5.

Yield: 36%. Mp: 180-181° C. (EtOH). $^1$H-NMR (300 MHz, DMSO-$d_6$): δ ppm 7.11-7.22 (m, 2H, Ar—$H_{5,6'}$), 7.32-7.43 (m, 2H, Ar—$H_{5',3''}$), 7.54-7.65 (m, 2H, Ar—$H_{6,3'}$), 7.70-7.78 (m, 2H, Ar—$H_{4'',5''}$), 8.18-8.20 (m, 2H, Ar—$H_{2,6''}$), 10.81 (s, 1H, NH), 12.19 (s, 1H, OH). HRMS (EI) m/z: calcd [M]$^+$, 393.0788 ($C_{20}H_{12}F_5NO_2^+$); found, 393.0784.

EXAMPLE 6

2',4'-difluoro-4-hydroxy-N-(3-(trifluoromethyl)phenyl)[1,1'-biphenyl]-3-carboxamide (compound 6)

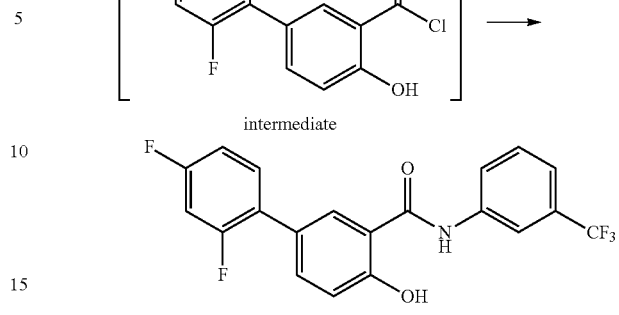

The synthesis method of compound 6:

Thionyl chloride (1 mL, 14 mmol) was added to disfunisal (0.9 g, 4 mmol) in anhydrous tetrahydrofuran (30 mL), and the mixture was refluxed under nitrogen atmosphere for 8 h. After cooling to room temperature, the mixture was steamed to give the intermediate by Dean-Stark apparatus, which residue was used directly in the next step. Freshly prepared intermediate was directly reacted with 3-(trifluoromethyl)aniline (0.5 mL, 4 mmol) in anhydrous tetrahydrofuran (30 mL) for 14 h. After removal of tetrahydrofuran, the reaction mixture was washed with ethyl acetate/hexane and the crude product was extracted in ethyl acetate. The organic layer was collect and dried over anhydrous $Na_2SO_4$, and then the solvent was evaporated. The crude product was washed and purified by crystallization from hot ethanol to afford compound 6.

Yield: 32%. Mp: 202-203° C. (EtOH). $^1$H-NMR (300 MHz, DMSO-$d_6$): δ ppm 7.10 (d, J=8.7 Hz, 1H, Ar—$H_5$), 7.20 (td, J=9, 2.7 Hz, 1H, Ar—$H_{6'}$), 7.37 (td, J=11.1, 2.4 Hz, 1H, Ar—$H_5$), 7.49 (d, J=7.8 Hz, 1H, Ar—$H_{6''}$), 7.57-7.65 (m, 3H, Ar—$H_{3',4'',5''}$), 7.95 (d, J=8.1 Hz, 1H, Ar—$H_6$), 8.05 (t, J=1.2 Hz, 1H, Ar—$H_2$), 8.21 (s, 1H, Ar—$H_{2''}$), 10.66 (s, 1H, NH), 11.70 (s, 1H, OH). HRMS (ET) m/z: calcd [M]$^+$, 393.0788 ($C_{20}H_{12}F_5NO_2^+$); found, 393.0787.

EXAMPLE 7

2',4'-difluoro-4-hydroxy-N-(4-(trifluoromethyl)phenyl)-[1,1'-biphenyl]-3-carboxamide (compound 7)

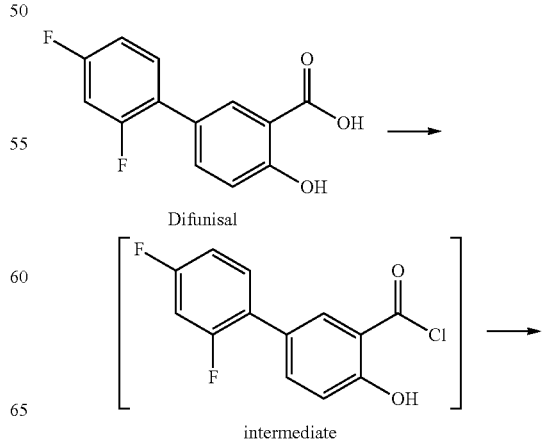

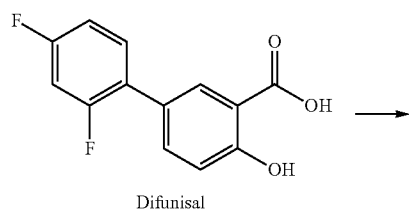

-continued

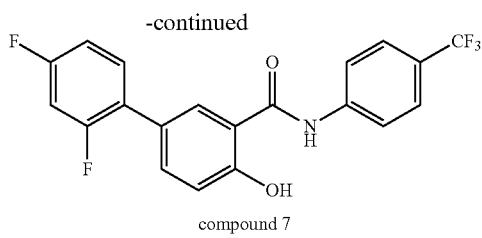

compound 7

The synthesis method of compound 7:

Thionyl chloride (1 mL, 14 mmol) was added to disfunisal (0.9 g, 4 mmol) in anhydrous tetrahydrofuran (30 mL), and the mixture was refluxed under nitrogen atmosphere for 8 h. After cooling to room temperature, the mixture was steamed to give the intermediate by Dean-Stark apparatus, which residue was used directly in the next step. Freshly prepared intermediate was directly reacted with 4-(trifluoromethyl)aniline (0.5 mL, 4 mmol) in anhydrous tetrahydrofuran (30 mL) for 14 h. After removal of tetrahydrofuran, the reaction mixture was washed with ethyl acetate/hexane and the crude product was extracted in ethyl acetate. The organic layer was collect and dried over anhydrous $Na_2SO_4$, and then the solvent was evaporated. The crude product was washed and purified by crystallization from hot ethanol to afford compound 7.

Yield: 44%. Mp: 227-228° C. (EtOH). $^1$H-NMR (300 MHz, DMSO-$d_6$): δ ppm 7.10 (d, J=8.4 Hz, 1H, Ar—$H_5$), 7.18 (td, J=13.7, 1.5 Hz, 1H, Ar—$H_{6'}$), 7.36 (td, J=9.3, 2.7 Hz, 1H, Ar—$H_{5'}$), 7.74 (d, J=9.0 Hz, 2H, Ar—$H_{3'',5''}$), 7.95 (d, J=8.4 Hz, 2H, Ar—$H_{2'',6''}$), 8.03 (s, 1H, Ar—$H_2$), 10.67 (s, 1H, NH), 11.66 (s, 1H, OH). HRMS (EI) m/z: calcd $[M]^+$, 393.0788 ($C_{20}H_{12}F_5NO_2^+$); found, 393.0791.

EXAMPLE 8

N-(3-ethynylphenyl)-2',4'-difluoro-4-hydroxy-[1,1'-biphenyl]-3-carboxamide (compound 8)

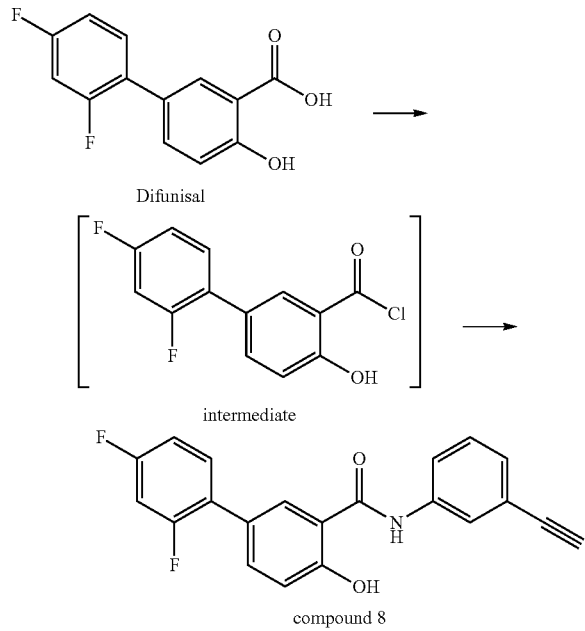

compound 8

The synthesis method of compound 8:

Thionyl chloride (1 mL, 14 mmol) was added to disfunisal (0.9 g, 4 mmol) in anhydrous tetrahydrofuran (30 mL), and the mixture was refluxed under nitrogen atmosphere for 8 h. After cooling to room temperature, the mixture was steamed to give the intermediate by Dean-Stark apparatus, which residue was used directly in the next step. Freshly prepared intermediate was directly reacted with 3-ethynylaniline (0.45 mL, 4 mmol) in anhydrous tetrahydrofuran (30 mL) for 14 h. After removal of tetrahydrofuran, the reaction mixture was washed with ethyl acetate/hexane and the crude product was extracted in ethyl acetate. The organic layer was collect and dried over anhydrous $Na_2SO_4$, and then the solvent was evaporated. The crude product was washed and purified by crystallization from hot ethanol to afford compound 8.

Yield: 38%. Mp: 215-216° C. (EtOH). $^1$H-NMR. (300 MHz, DMSO-$d_6$): δ ppm 7.09 (d, J=8.7 Hz, 1H, Ar—$H_5$), 7.17-7.26 (m, 2H, Ar—$H_{4'',6'}$), 7.33-7.41 (m, 2H, Ar—$H_{5',5''}$), 7.57-7.65 (m, 2H, Ar—$H_{6,3'}$), 7.70-7.73 (m, 1H, Ar—$H_{6''}$), 7.89 (t, J=1.8 Hz, 1H, Ar—$H_2$), 8.05 (t, J=1.2 Hz, 1H, Ar—$H_{2''}$), 10.48 (s, 1H, NH), 11.79 (s, 1H, OH). HRMS (EI) m/z: calcd $[M]^+$, 348.0836 ($C_{21}H_{12}F_2NO_2^+$); found, 348.0835.

EXAMPLE 9

N-(3-cyanophenyl)-2',4'-difluoro-4-hydroxy-[1,1'-biphenyl]-3-carboxamide (compound 9)

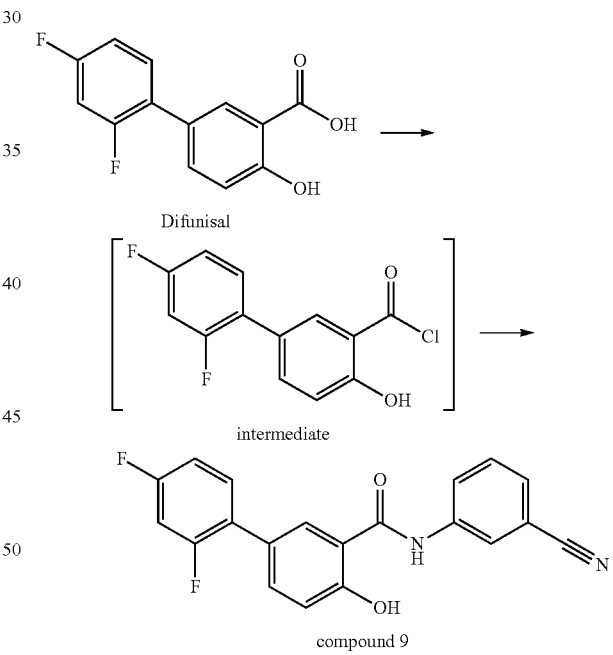

compound 9

The synthesis method of compound 9:

Thionyl chloride (1 mL, 14 mmol) was added to disfunisal (0.9 g, 4 mmol) in anhydrous tetrahydrofuran (30 mL), and the mixture was refluxed under nitrogen atmosphere for 8 h. After cooling to room temperature, the mixture was steamed to give the intermediate by Dean-Stark apparatus, which residue was used directly in the next step. Freshly prepared intermediate was directly reacted with 3-aminobenzonitrile (0.47 g, 4 mmol) in anhydrous tetrahydrofuran (30 mL) for 14 h. After removal of tetrahydrofuran, the reaction mixture was washed with ethyl acetate/hexane and the crude product was extracted in ethyl acetate. The organic layer was collect and dried over anhydrous Na₂SO₄, and then the solvent was evaporated. The crude product was washed and purified by crystallization from hot ethanol to afford compound 9.

Yield: 51%. Mp: 229-230° C. (EtOH). ¹H-NMR (300 MHz, DMSO-d₆): δ ppm 7.10 (d, J=8.4 Hz, 1H, Ar—H₅), 7.16-7.22 (m, 1H, Ar—H₆'), 7.35 (td, J=10.35, 2.7 Hz, 1H, Ar—H₅'), 7.55-7.63 (m, 4H, Ar—H₆,₃',₄",₅"), 7.96-8.00 (m, 1H, Ar—H₆"), 8.02 (t, J=0.9 Hz, 1H, Ar—H₂), 8.21 (t, J=0.9 Hz, 1H, Ar—H₂"), 10.63 (s, 1H, NH), 11.66 (s, 1H, OH). HRMS (EI) m/z: calcd [M]⁺, 350.0867 ($C_{20}H_{12}F_2N_2O_2^+$); found, 350.0857.

EXAMPLE 10

N-(4-cyanophenyl)-2',4'-difluoro-4-hydroxy-[1,1'-biphenyl]-3-carboxamide (compound 10)

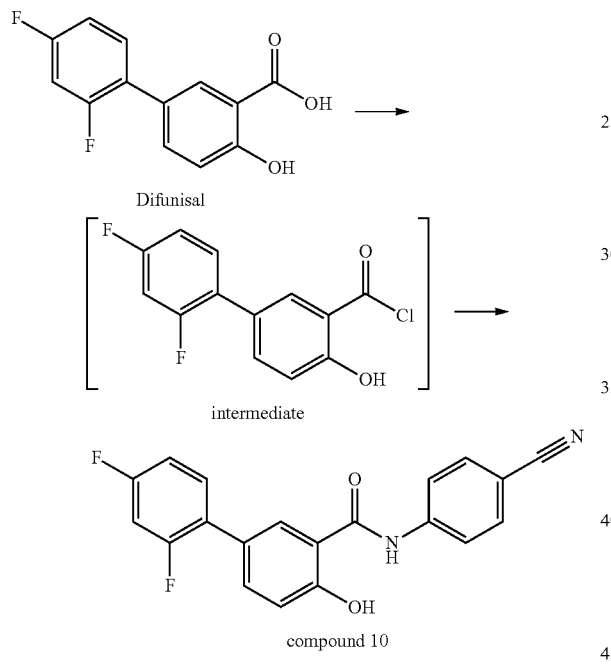

The synthesis method of compound 10:

Thionyl chloride (1 mL, 14 mmol) was added to disfunisal (0.9 g, 4 mmol) in anhydrous tetrahydrofuran (30 mL), and the mixture was refluxed under nitrogen atmosphere for 8 h. After cooling to room temperature, the mixture was steamed to give the intermediate by Dean-Stark apparatus, which residue was used directly in the next step. Freshly prepared intermediate was directly reacted with 4-aminobenzonitrile (0.47 g, 4 mmol) in anhydrous tetrahydrofuran (30 mL) for 14 h. After removal of tetrahydrofuran, the reaction mixture was washed with ethyl acetate/hexane and the crude product was extracted in ethyl acetate. The organic layer was collect and dried over anhydrous Na₂SO₄, and then the solvent was evaporated. The crude product was washed and purified by crystallization from hot ethanol to afford compound 10.

Yield: 54%. Mp: 189-190° C. (EtOH). ¹H-NMR (300 MHz, DMSO-d₆): δ ppm 7.19 (td, J=8.4, 0.9 Hz, 1H, Ar—H₆'), 7.35 (td, J=10.2, 2.4 Hz, 1H, Ar—H₅'), 7.55-7.63 (m, 2H, Ar—H₆,₃'), 7.81-7.84 (m, 2H, Ar—H₃",₅"), 7.91-7.94 (m, 1H, Ar—H₂",₆"), 7.98 (t, J=1.2 Hz, 1H, Ar—H₂), 10.70 (s, 1H, NH), 11.55 (s, 1H, OH). HRMS (EI) m/z: calcd [M]⁺, 350.0867 ($C_{20}H_{12}F_2N_2O_2^+$); found, 350.0872.

EXAMPLE 11

N-(3,4-dimethoxyphenyl)-2',4'-difluoro-4-hydroxy-[1,1'-biphenyl]-3-carboxamid (compound 11)

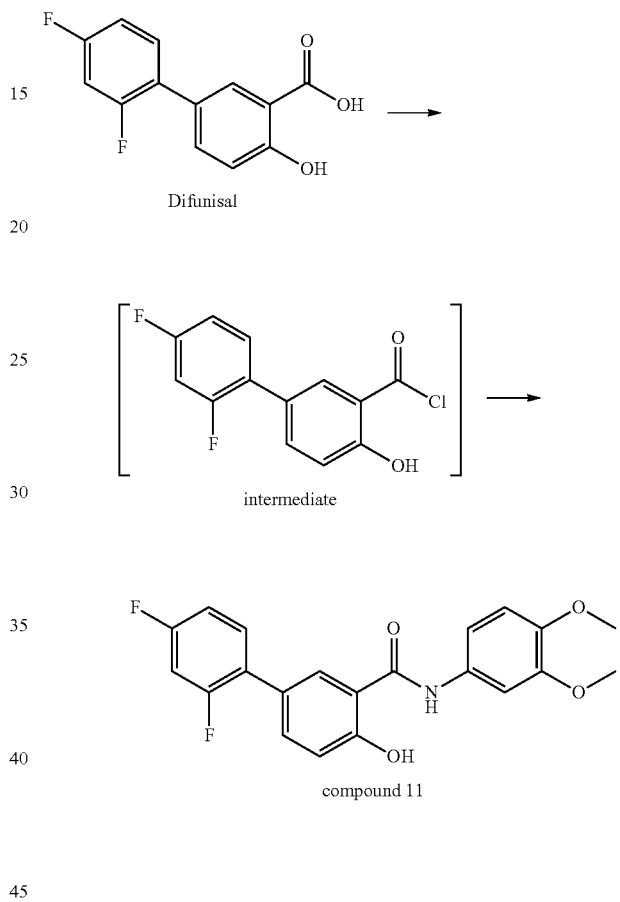

The synthesis method of compound 11:

Thionyl chloride (1 mL, 14 mmol) was added to disfunisal (0.9 g, 4 mmol) in anhydrous tetrahydrofuran (30 mL), and the mixture was refluxed under nitrogen atmosphere for 8 h. After cooling to room temperature, the mixture was steamed to give the intermediate by Dean-Stark apparatus, which residue was used directly in the next step. Freshly prepared intermediate was directly reacted with 3,4-dimethoxyaniline (0.61 g, 4 mmol) in anhydrous tetrahydrofuran (30 mL) for 14 h. After removal of tetrahydrofuran, the reaction mixture was washed with ethyl acetate/hexane and the crude product was extracted in ethyl acetate. The organic layer was collect and dried over anhydrous Na₂SO₄, and then the solvent was evaporated. The crude product was washed and purified by crystallization from hot ethanol to afford compound 11.

Yield: 34%. Mp: 186-187° C. (EtOH). ¹H-NMR (300 MHz, DMSO-d₆): δ ppm 3.75 (s, 3H, OCH₃), 3.76 (s, 3H, OCH₃), 6.95 (d, J=9 Hz, 1H, Ar—H₂"), 7.07 (d, J=6.6 Hz, 1H, Ar—H₅), 7.17-7.25 (m, 2H, Ar—H₆',₅"), 7.31-7.39 (m, 2H, Ar—H₅',₆"), 7.56-7.66 (m, 2H, Ar—H₆,₃'), 8.11 (s, 1H, Ar—H$_2$), 10.33 (s, 1H, NH), 12.12 (s, 1H, OH). HRMS (EI) m/z: calcd [M]$^+$, 385.1126 (C$_{21}$H$_{17}$F$_2$NO$_4$$^+$); found, 385.1124.

EXAMPLE 12

2',4'-difluoro-4-hydroxy-N-(3-methoxyphenyl)-[1,1'-biphenyl]-3-carboxamide (compound 12)

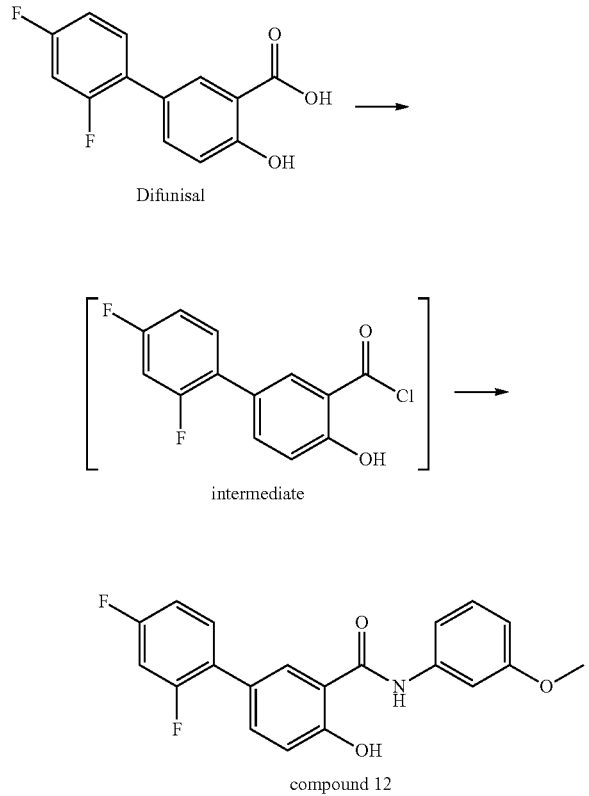

The synthesis method of compound 12:

Thionyl chloride (1 mL, 14 mmol) was added to disfunisal (0.9 g, 4 mmol) in anhydrous tetrahydrofuran (30 mL), and the mixture was refluxed under nitrogen atmosphere for 8 h. After cooling to room temperature, the mixture was steamed to give the intermediate by Dean-Stark apparatus, which residue was used directly in the next step. Freshly prepared intermediate was directly reacted with 3-methoxyaniline (0.46 g, 4 mmol) in anhydrous tetrahydrofuran (30 mL) for 14 h. After removal of tetrahydrofuran, the reaction mixture was washed with ethyl acetate/hexane and the crude product was extracted in ethyl acetate. The organic layer was collect and dried over anhydrous Na$_2$SO$_4$, and then the solvent was evaporated. The crude product was washed and purified by crystallization from hot ethanol to afford compound 12.

Yield: 32%. Mp: 187-188° C. (EtOH). $^1$H-NMR (300 MHz, DMSO-d$_6$): δ ppm 3.76 (s, 3H, OCH$_3$), 6.70-6.74 (m, 1H, Ar—H$_{5''}$), 7.08 (d, J=8.4 Hz, 1H, Ar—H$_5$), 7.16-7.39 (m, 4H, Ar—H$_{6',2'',4'',6''}$) 7.57-7.65 (m, 2H, Ar—H$_{6,3'}$), 8.07 (s, 1H, Ar—H$_2$), 10.39 (s, 1H, NH), 11.90 (s, 1H, OH). HRMS (EI) m/z: calcd [M]$^+$, 355.100 (C$_{20}$H$_{15}$F$_2$NO$_3$$^+$); found, 355.1014.

The compounds 13-24 are prepared by the compounds 1-12 in the present invention. The synthesis methods are showed as example 13-24:

EXAMPLE 13

3-(4-chloro-2-fluorophenyl)-6-(2,4-difluorophenyl)-2H-benzo[e][1,3]oxazine-2,4(3H)-dione (compound 13)

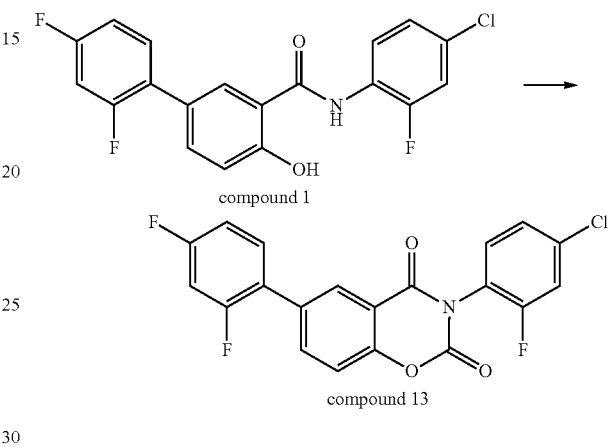

The synthesis method of compound 13:

A solution of methyl chloroformate (1.2 mL, 12 mmol) was added drop wised to a stirred solution of compound 1 (1.5 g, 4 mmol) in dry anhydrous tetrahydrofuran/pyridine (30 mL) at 0° C. The mixture was refluxed for 2.5 h. After 10 h stirring at room temperature, the pH value of the mixture was adjusted to pH=6 by 5% HCl$_{(aq)}$. The mixture was cooled to obtain crystalline compound on an ice bath for 2-3 h. After cooling, precipitated crystals were filtered off and washed with diluted HCl and water. The crude product was purified by crystallization from hot ethanol to afford compound 13.

Yield: 11%. Mp: 176-177° C. (EtOH). $^1$H-NMR (300 MHz, DMSO-d$_6$): δ ppm 7.23 (td, J=8.4, 2.5 Hz, 1H, Ar—H$_{6'}$), 7.23 (td, J=10.4, 2.7 Hz, 1H, Ar—H$_{5'}$), 7.48-7.52 (m, 1H, Ar—H$_{6''}$), 7.63-7.75 (m, 4H, Ar—H$_{5,3',3'',5''}$), 8.05 (dt, J=8.4, 1.5 Hz, 1H, Ar—H$_6$), 8.10 (t, J=1.8 Hz, 1H, Ar—H$_2$), HRMS (EI) m/z: calcd [M]$^+$, 403.0223 (C$_{20}$H$_9$ClF$_3$NO$_3$$^+$); found, 403.0229.

EXAMPLE 14

3,6-bis(2,4-difluorophenyl)-2H-benzo[e][1,3]oxazine-2,4(3H)-dione (compound 14)

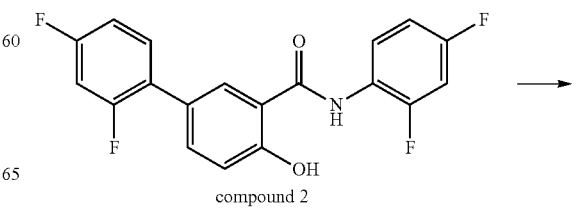

23

-continued

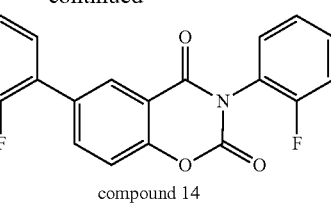
compound 14

The synthesis method of compound 14:

A solution of methyl chloroformate (1.2 mL, 12 mmol) was added drop wised to a stirred solution of compound 2 (1.44 g, 4 mmol) in dry anhydrous tetrahydrofuranipyridine (30 mL) at 0° C. The mixture was refluxed for 3 h. After 10 h stirring at room temperature, the pH value of the mixture was adjusted to pH=6 by 5% $HCl_{(aq)}$. The mixture was cooled to obtain crystalline compound on an ice bath for 2-3 h. After cooling, precipitated crystals were filtered off and washed with diluted HCl and water. The crude product was purified by crystallization from hot ethanol to afford compound 14.

Yield: 61%. Mp: 155-156° C. (EtOH). $^1$H-NMR (300 MHz, DMSO-$d_6$): δ ppm 7.20-7.33 (m, 2H, 7.42 (td, J=9.7, 1.5 Hz, Ar—$H_{5'}$), 7.54 (td, J=9.7, 2.1 Hz, 1H, Ar—$H_{6'}$), 7.65-7.74 (m, 3H, Ar—$H_{5,3',3''}$), 8.03-8.10 (m, 2H, Ar—$H_{2,6}$). HRMS (EI) m/z: calcd $[M]^+$, 387.0519 ($C_{20}H_9F_4NO_3^+$); found, 387.0518.

EXAMPLE 15

6-(2,4-difluorophenyl)-3-3,4-difluorophenyl)-2H-benzo[e][1,3]oxazine-2,4(3H)-dione (compound 15)

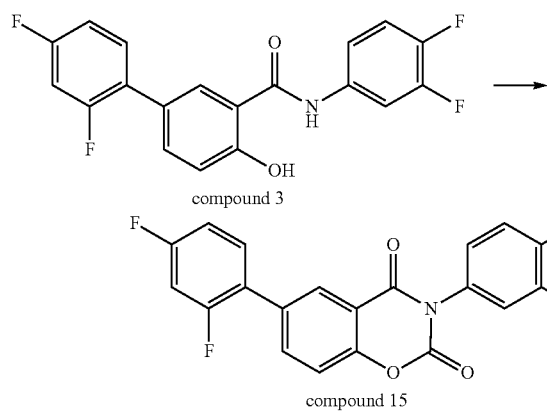

The synthesis method of compound 15:

A solution of methyl chloroformate (1.2 mL, 12 mmol) was added drop wised to a stirred solution of compound 3 (1.44 g, 4 mmol) in dry anhydrous tetrahydrofuran/pyridine (30 mL) at 0° C. The mixture was refluxed for 3 h. After 10 h stirring at room temperature, the pH value of the mixture was adjusted to pH=6 by 5% $HCl_{(aq)}$. The mixture was cooled to obtain crystalline compound on an ice bath for 2-3 h. After cooling, precipitated crystals were filtered off and washed with diluted HCl and water. The etude product was purified by crystallization from hot ethanol to afford compound 15.

Yield: 25%. Mp: 193-194° C. (EtOH). $^1$H-NMR (300 MHz, DMSO-$d_6$): δ ppm 7.20-7.23 (m, 1H, Ar—$H_{6'}$), 7.34-7.45 (m, 2H, Ar—$H_{5',2''}$), 7.57-7.73 (m, 4H, Ar—$H_{5,3',5'',6''}$), 8.03-8.04 (m, 1H, Ar—$H_6$), 8.08 (t, J=1.8 Hz, 1H, Ar—$H_2$). HRMS (EI) m/z: calcd $[M]^+$, 387.0519 ($C_{20}H_9F_4NO_3^+$); found, 387.0522.

EXAMPLE 16

6-(2,4-difluorophenyl)-3-(2,5-difluorophenyl)-2H-benzo[e][1,3]oxazine-2,4(3H)-dione (compound 16)

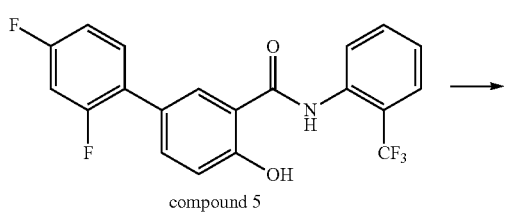

The synthesis method of compound 16:

A solution of methyl chloroformate (1.2 mL, 12 mmol) was added drop wised to a stirred solution of compound 4 (1.44 g, 4 mmol) in dry anhydrous tetrahydrofuran/pyridine (30 mL) at 0° C. The mixture was refluxed for 3 h. After 10 h stirring at room temperature, the pH value of the mixture was adjusted to pH=6 by 5% $HCl_{(aq)}$. The mixture was cooled to obtain crystalline compound on an ice bath for 2-3 h. After cooling, precipitated crystals were filtered off and washed with diluted HCl and water. The crude product was purified by crystallization from hot ethanol to afford compound 16.

Yield: 15%. Mp: 144-145° C. (EtOH). $^1$H-NMR (300 MHz, DMSO-$d_6$): δ ppm 7.23 (td, J=8.4, 2.4 Hz, 1H, Ar—$H_{6'}$), 7.37-7.58 (m, 4H, Ar—$H_{5',3'',4'',6''}$), 7.65-7.73 (m, 2H, Ar—$H_{5,3'}$), 8.03-8.11 (m, 2H, Ar—$H_{2,6}$). HRMS (EI) m/z: calcd $[M]^+$, 387.0519 ($C_{20}H_9F_4NO_3^+$); found, 387.0516.

EXAMPLE 17

6-(2,4-difluorophenyl)-3-(2-(trifluoromethy)phenyl)-2H-benzo[e][1,3]oxazine-2,4(3H)-dione (compound 17)

compound 5

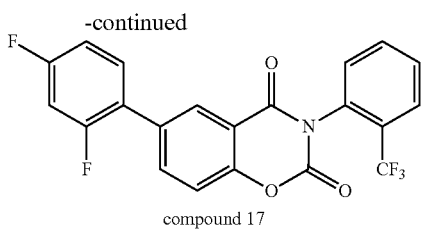

compound 17

The synthesis method of compound 17:

A solution of methyl chloroformate (1.2 mL, 12 mmol) was added drop wised to a stirred solution of compound 5 (1.56 g, 4 mmol) in dry anhydrous tetrahydrofuran/pyridine (30 mL) at 0° C. The mixture was refluxed for 3 h. After 10 h stirring at room temperature, the pH value of the mixture was adjusted to pH=6 by 5% $HCl_{(aq)}$. The mixture was cooled to obtain crystalline compound on an ice bath for 2-3 h. After cooling, precipitated crystals were filtered off and washed with diluted HCl and water. The crude product was purified by crystallization from hot ethanol to afford compound 17.

Yield: 31%. Mp: 200-201° C. (EtOH). $^1$H-NMR (300 MHz, DMSO-$d_6$): δ ppm 7.23 (td, J=9.3, 2.4 Hz, 1H, Ar—H$_{6''}$), 7.42 (td, J=10.2, 2.4 Hz, 1H, Ar—H$_{5'}$), 7.68-7.82 (m, 4H, Ar—H$_{5,3',3'',6''}$), 7.89-7.95 (m, 2H, Ar—H$_{4'',5''}$), 8.05-8.11 (m, 2H, Ar—H$_{2,6}$). HRMS (EI) m/z: calcd [M]$^+$, 419.0581 ($C_{21}H_{10}F_5NO_3^+$); found, 419.0586.

EXAMPLE 18

6-(2,4-difluorophenyl)-3-(3-(trifluoromethyl)phenyl)-2H-benzo[e][1,3]oxazine-2,4(3H)-dione (compound 18)

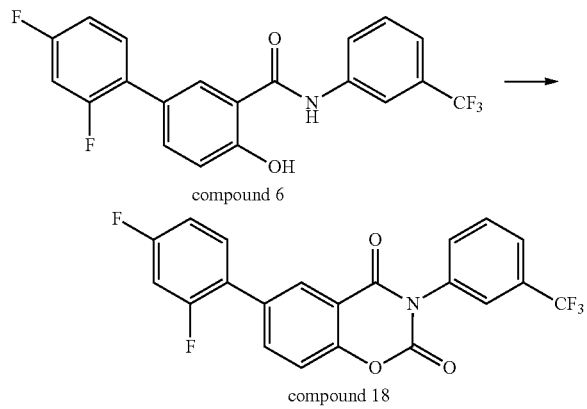

The synthesis method of compound 18:

A solution of methyl chloroformate (1.2 mL, 12 mmol) was added drop wised to a stirred solution of compound 6 (1.56 g, 4 mmol) in dry anhydrous tetrahydrofuran/pyridine (30 mL) at 0° C. The mixture was refluxed for 3 h. After 10 h stifling at room temperature, the pH value of the mixture was adjusted to pH=6 by 5% $HCl_{(aq)}$. The mixture was cooled to obtain crystalline compound on an ice bath for 2-3 h. After cooling, precipitated crystals were filtered off and washed with diluted HCl and water. The crude product was purified by crystallization from hot ethanol to afford compound 18.

Yield: 13%, Mp: 165-166° C. (EtOH). $^1$H-NMR (300 MHz, DMSO-$d_6$): δ ppm 7.24 (td, J=7.5, 2.1 Hz, 1H, Ar—H$_{6'}$), 7.42 (td, J=10.1, 2.7 Hz, 1H, Ar—H$_{5'}$), 7.64-7.73 (m, 2H, Ar—H$_{5,3'}$), 7.78-7.80 (m, 2H, Ar—H$_{4'',6''}$), 7.85-7.88 (m, 1H, Ar—H$_{5''}$), 7.91 (s, 1H, Ar—H$_{2''}$), 8.03 (dt, J=9.3, 1.5 Hz, 1H, Ar—H$_6$), 8.08 (t, J=1.8 Hz, 1H, Ar—H$_2$). HRMS (EI) m/z: calcd [M]$^+$, 419.0581. ($C_{21}H_{10}F_5NO_3^+$); found, 419.0590.

EXAMPLE 19

6-(2,4-difluorophenyl)-3-(4-(trifluoromethyl)phenyl)-2H-benzo[e][1,3]oxazine-2,4(3H)-dione (compound 19)

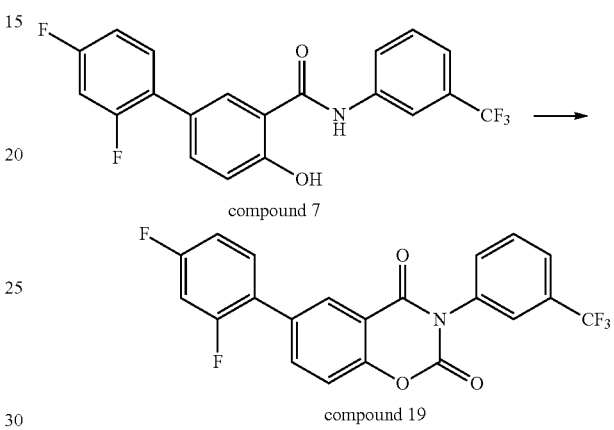

The synthesis method of compound 19:

A solution of methyl chloroformate (1.2 mL, 12 mmol) was added drop wised to a stirred solution of compound 7 (1.56 g, 4 mmol) in dry anhydrous tetrahydrofuran/pyridine (30 mL) at 0° C. The mixture was refluxed for 3 h. After 10 h stirring at room temperature, the pH value of the mixture was adjusted to pH=6 by 5% $HCl_{(aq)}$. The mixture was cooled to obtain crystalline compound on an ice bath for 2-3 h. After cooling, precipitated crystals were filtered off and washed with diluted HCl and water. The crude product was purified by crystallization from hot ethanol to afford compound 19.

Yield: 11%. Mp: 209-210° C. (EtOH). $^1$H-NMR (300 MHz, DMSO-$d_6$): δ ppm 7.24 (td, J=9, 1.2 Hz, 1H, Ar—H$_{6'}$), 7.42 (td, J=10.2, 2.4 Hz, 1H, Ar—H$_{5'}$), 7.63-7.73 (m, 4H, Ar—H$_{3,5,3'',5''}$), 7.93 (d, J=8.4 Hz, 2H, Ar—H$_{2'',6''}$), 8.03 (dt, J=8.7, 2.1 Hz, 1H, Ar—H$_6$), 8.08 (t, J=1.5 Hz, 1H, Ar—H$_2$). HRMS (EI) m/z: calcd [M]$^+$, 419.0581 ($C_{21}H_{10}F_5NO_3^+$); found, 419.0584.

EXAMPLE 20

6-(2,4-difluorophenyl)-3-(3-ethynylphenyl)-2H-benzo[e][1,3]oxazine-2,4(3H)-dione (compound 20)

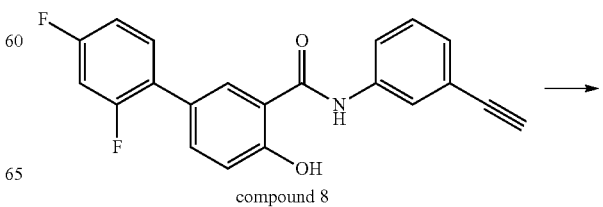

compound 8

27
-continued

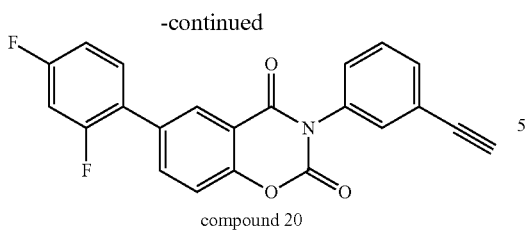
compound 20

The synthesis method of compound 20:

A solution of methyl chloroformate (1.2 mL, 12 mmol) was added drop wised to a stirred solution of compound 8 (1.39 g, 4 mmol) in dry anhydrous tetrahydrofuran/pyridine (30 mL) at 0° C. The mixture was refluxed for 3 h. After 10 h stirring at room temperature, the pH value of the mixture was adjusted to pH=6 by 5% $HCl_{(aq)}$. The mixture was cooled to obtain crystalline compound on an ice bath for 2-3 h. After cooling, precipitated crystals were filtered off and washed with diluted HCl and water. The crude product was purified by crystallization from hot ethanol to afford compound 20.

Yield: 14%. Mp: 195-196° C. (EtOH). $^1$H-NMR (300 MHz, DMSO-d$_6$): δ ppm 7.23 (td, J=8.3, 2.7 Hz, 1H, Ar—H$_{6'}$), 7.42 (td, J=10.2, 2.4 Hz, 1H, Ar—H$_{5'}$), 7.48-7.73 (m, 6H, Ar—H$_{5,3',2'',4'',5'',6''}$), 7.99-8.04 (m, 1H, Ar—H$_6$), 8.07 (t, J=1.8 Hz, 1H, Ar—H$_2$). HRMS (EI) m/z: calcd [M]$^+$, 375.0707 ($C_{21}H_{11}F_2NO_3^+$); found, 375.0708.

EXAMPLE 21

3-(6-(2,4-difluorophenyl)-2,4-dioxo-2H-benzo[e][1,3]oxazin-3(4H)-yl)benzonitrile (compound 21)

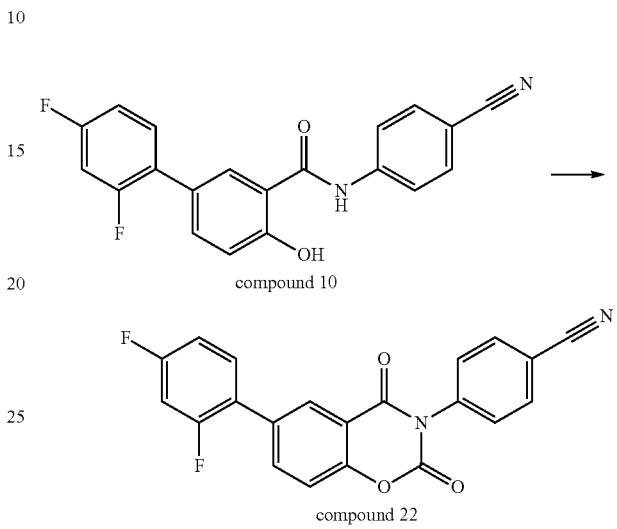

The synthesis method of compound 21:

A solution of methyl chloroformate (1.2 mL, 12 mmol) was added drop wised to a stirred solution of compound 9 (1.4 g, 4 mmol) in dry anhydrous tetrahydrofuran/pyridine (30 mL) at 0° C. The mixture was refluxed for 3 h. After 10 h stirring at room temperature, the pH value of the mixture was adjusted to pH=6 by 5% $1HCl_{(aq)}$. The mixture was cooled to obtain crystalline compound on an ice bath for 2-3 h. After cooling, precipitated crystals were filtered off and washed with diluted HCl and water. The crude product was purified by crystallization from hot ethanol to afford compound 21.

Yield: 49%. Mp: 209-210° C. (EtOH). $^1$H-NMR (300 MHz, DMSO-d$_6$): δ ppm 7.21-7.27 (m, 1H, Ar—H$_{6'}$), 7.42 (td, J=10.5, 2.4 Hz, 1H, Ar—H$_{5'}$), 7.64-7.86 (m, 5H, Ar—H$_{5,3',4'',5'',6''}$) 7.96-8.05 (m, 2H, Ar—H$_{6,2''}$), 8.09 (t, J=1.8 Hz, 1H, Ar—H$_2$). HRMS (EI) m/z: calcd [M]$^+$, 376.0659 ($C_{21}H_{10}F_2N_2O_3^+$); found, 375.0622.

EXAMPLE 22

4-(6-(2,4-difluorophenyl)-2,4-dioxo-2H-benzo[e][1,3]oxazin-3(4H)-yl)benzonitrile (compound 22)

The synthesis method of compound 22:

A solution of methyl chloroformate (1.2 mL, 12 mmol) was added drop wised to a stirred solution of compound 10 (1.4 g, 4 mmol) in dry anhydrous tetrahydrofuran/pyridine (30 mL) at 0° C. The mixture was refluxed for 3 h. After 10 h stirring at room temperature, the pH value of the mixture was adjusted to pH=6 by 5% $HCl_{(aq)}$. The mixture was cooled to obtain crystalline compound on an ice bath for 2-3 h. After cooling, precipitated crystals were filtered off and washed with diluted HCl and water. The crude product was purified by crystallization from hot ethanol to afford compound 22.

Yield: 22%. Mp: 203-204° C. (EtOH). $^1$H-NMR (300 MHz, DMSO-d$_6$): δ ppm 7.24 (td, J=8.7, 0.9 Hz, 1H, Ar—H$_{6'}$), 7.42 (td, J=10.1, 2.7 Hz, 1H, Ar—H$_{5'}$), 7.63-7.73 (m, 4H, Ar—H$_{5,3',3'',4''}$), 8.01-8.08 (m, 4H, Ar—H$_{2,6,2'',6''}$). HRMS (EI) m/z: calcd [M]$^+$, 376.0659 ($C_{21}H_{10}F_2N_2O_3^+$); found, 375.0655.

EXAMPLE 23

6-(2,4-difluorophenyl)-3-(3,4-dimethoxyphenyl)-2H-benzo[e][1,3]oxazine-2,4(3H)-dione (compound 23)

-continued

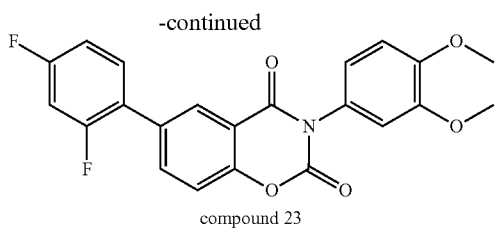
compound 23

The synthesis method of compound 23:

A solution of methyl chloroformate (1.2 mL, 12 mmol) was added drop wised to a stirred solution of compound 11 (1.54 g, 4 mmol) in dry anhydrous tetrahydrofuran/pyridine (30 mL) at 0° C. The mixture was refluxed for 3 h. After 10 h stirring at room temperature, the pH value of the mixture was adjusted to pH=6 by 5% $HCl_{(aq)}$. The mixture was cooled to obtain crystalline compound on an ice bath for 2-3 h. After cooling, precipitated crystals were filtered off and washed with diluted HCl and water. The crude product was purified by crystallization from hot ethanol to afford compound 23.

Yield: 43%. Mp: 198-199° C. (EtOH). $^1$H-NMR (300 MHz, DMSO-$d_6$): δ ppm 3.72 (s, 3H, $OCH_3$), 3.81 (s, 3H, $OCH_3$), 6.96 (dd, J=8.5, 2.1 Hz, 1H Ar—$H_{5''}$), 7.04-7.09 (m, 2H, Ar—$H_{2'',6''}$), 7.42 (td, J=8.3, 2.7 Hz, 1H, Ar—$H_{6'}$), 7.61 (d, J=8.4 Hz, 1H, Ar—$H_5$), 7.65-7.73 (m, 1H, Ar—$H_{3'}$), 7.98-8.02 (m, 1H, Ar—$H_5$), 8.07 (t, J=1.5 Hz, 1H, Ar—$H_2$). HRMS (EI) m/z: calcd $[M]^+$, 411.0918 ($C_{22}H_{15}F_2NO_5^+$); found, 411.0917.

EXAMPLE 24

6-(2,4-difluorophenyl)-3-(3-methoxyphenyl)-2H-benzo[e][1,3]oxazine-2,4(3H)-dione (compound 24)

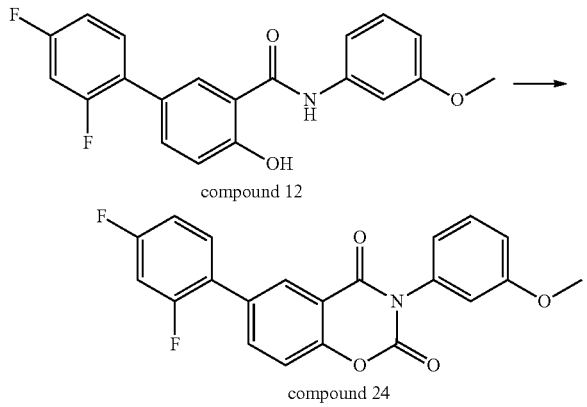

The synthesis method of compound 24:

A solution of methyl chloroformate (1.2 mL, 12 mmol) was added drop wised to a stirred solution of compound 12 (1.42 g, 4 mmol) in dry anhydrous tetrahydrofuran/pyridine (30 mL) at 0□. The mixture was refluxed for 3 h. After 10 h stirring at room temperature, the pH value of the mixture was adjusted to pH=6 by 5% $HCl_{(aq)}$. The mixture was cooled to obtain crystalline compound on an ice bath for 2-3 h. After cooling, precipitated crystals were filtered off and washed with diluted HCl and water. The crude product was purified by crystallization from hot ethanol to afford compound 24.

Yield: 12%. Mp: 160-161° C. (EtOH). $^1$H-NMR (300 MHz, DMSO-$d_6$): δ ppm 3.77 (s, 3H, $OCH_3$), 6.99-7.07 (m, 2H, Ar—$H_{4'',5''}$), 7.20-7.27 (m, 1H, Ar—$H_{6'}$), 7.38-7.45 (m, 2H, Ar—$H_{5',6'}$), 7.23-7.60 (m, 2H, Ar—$H_{5,3'}$), 7.98-8.03 (m, 1H, Ar—$H_6$), 8.07 (t, J=1.8 Hz, 1H, Ar—$H_2$). HRMS (EI) m/z: calcd $[M]^+$, 381.0813 ($C_{21}H_{13}F_2NO_4^+$); found, 381.0806.

The following examples is the activity of compounds 1 to 24 of the examples 1 to 24:

EXAMPLE 25

The Pharmacological Activity Test and Result

The compounds 1 to 24 of the present invention is tested by three pharmacological activity tests as follows: (1) MTT assay to test the RAW264.7 cell (murine monocyte/macrophage cell line) viability; (2) Tartrate-resistant acid phosphatase (TRAP) staining and activity analysis to investigate the cell differentiation activity; (3) The activity test of bone resorption (Pit formation assay). By these testes, the biphenyl benzamide-derived derivatives containing pharmaceutical composition, which comprises the formula I compound, were proved to perform effects of inhibition on osteoclastogenesis.

The synthesized difunisal derivatives, compounds 1 to 24, were pharmacologically tested to be identified the relationship between their structure and activity. Cell viability was measured by MTT assay in RAW 264.7 cells upon treatment with compounds at 5 μM. $CC_{50}$ is the cytotoxic concentration that produces 50% ($CC_{50}$) cell death. As shown in Table 3, the cell viability was more than 90% upon treatment with compounds at 5 μM. The multinucleated osteoclasts could be formed by RANKL-induced macrophage cell line RAW267. RAW 264.7 cells were cultured with the indicated in the presence of drug and RANKL (100 ng/mL). Numbers of TRAP-positive ($TRAP^+$) multinucleated cells (MNCs) were counted in the presence of RANKL to identify the relationship between osteoclast and bone formation. To avoid the effect of cell viability, the concentration of synthesized compounds was 5 μM, and the result was showed in Table 4. Some of the derivatives perform more than 50% inhibitory activity on RANKL-induced osteoclast differentiation, wherein the compound 4, compound 9, compound 16 and compound 18 perform 67.32±4.38%, 71.32±3.39%, 86.84±1.74% and 62.92±2.65% inhibitory activity of TRAP-positive ($TRAP^+$) multinucleated cells (MNCs) formation. The compound 16 performed the best inhibitory effect in the TRAP staining. The compound 16 was a derivate from compound 4 and its structure was related to compound 4. Therefore, the compound 4 and 16 were performed by TRAP assay to evaluate the effect on osteoclast differentiation by different concentration of compounds. As shown in FIG. 1A, compound 4 and 16 performed TRAP inhibitory activity, the $IC_{50}$ were 3.89 μM and <2.5 μM, respectively. According to above result, it can be speculated that: (1) Due to different substitutes on benzene ring of difunisal, the inhibitory ability of RANKL-induced osteoclast differentiation would be different. (2) Due to the electron-withdrawing group substitutes of $R_1$ and $R_4$ on benzene ring, or electron-withdrawing group substitutes derivatives of R2 on benzene ring, such as compound 4. ($R_1$=F and $R_4$=F), compound 6 ($R_2$=$CF_3$), compound 9 ($R_2$=CN) and compound 16 ($R_1$=F and $R_4$=F), (3) compound 4 ($R_1$=F and $R_4$=F) and compound 6 ($R_2$=$CF_3$), a cyclic derivate compound 16 ($R_1$=F and $R_4$=F) and compound 18 ($R_2$=$CF_3$), the inhibitory activity would be stronger. FIG. 2 showed the effect on RAW264.7 cell differentiation by compound 4 and 16 with or without the presence of RANKL.

EXAMPLE 26

Effect on Inhibition Resorption of Osteoclast by Compounds 1~24

Figure 1B:
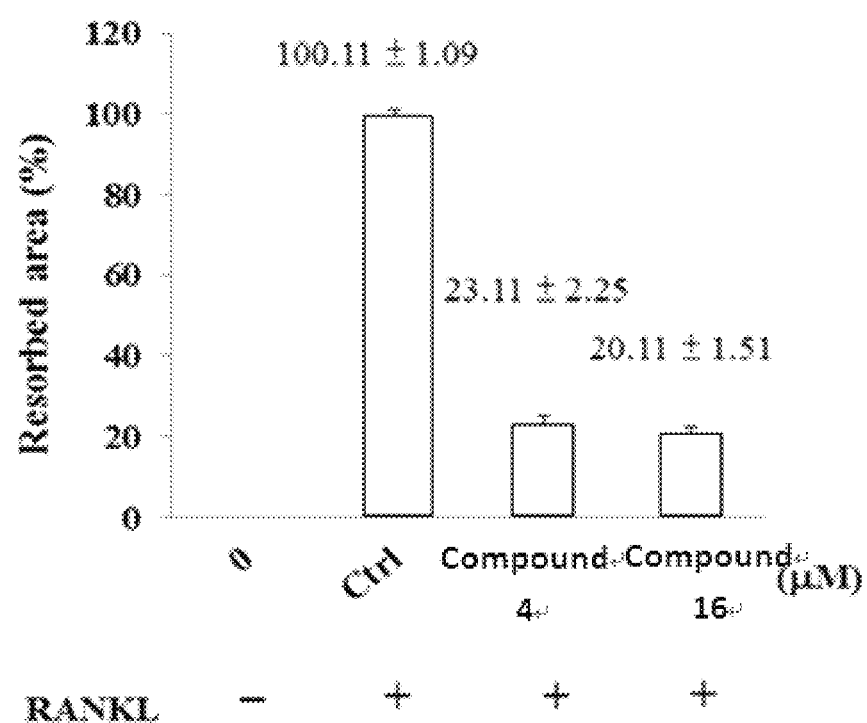
FIG. 1B shows the effects of different concentration of compound 4 and compound 16 on the bone resorption activity.
Figure 2A:
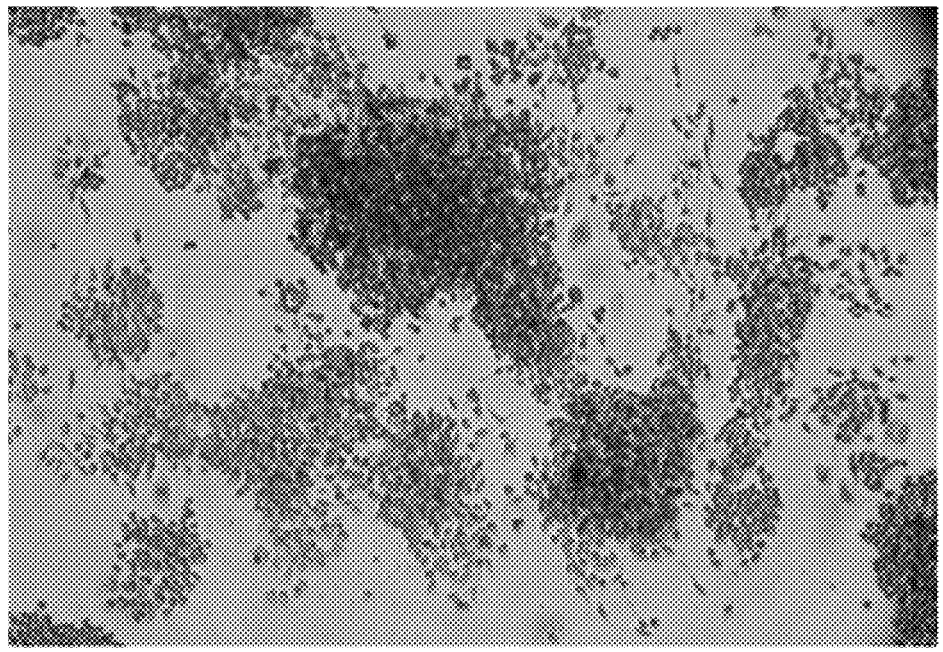
FIG. 2A shows the osteoclast differentiation of RAW264.7; RAW264.7 cells which were cultured without the compound 4 and compound 16 without the presence of RANKL.
Figure 2B:
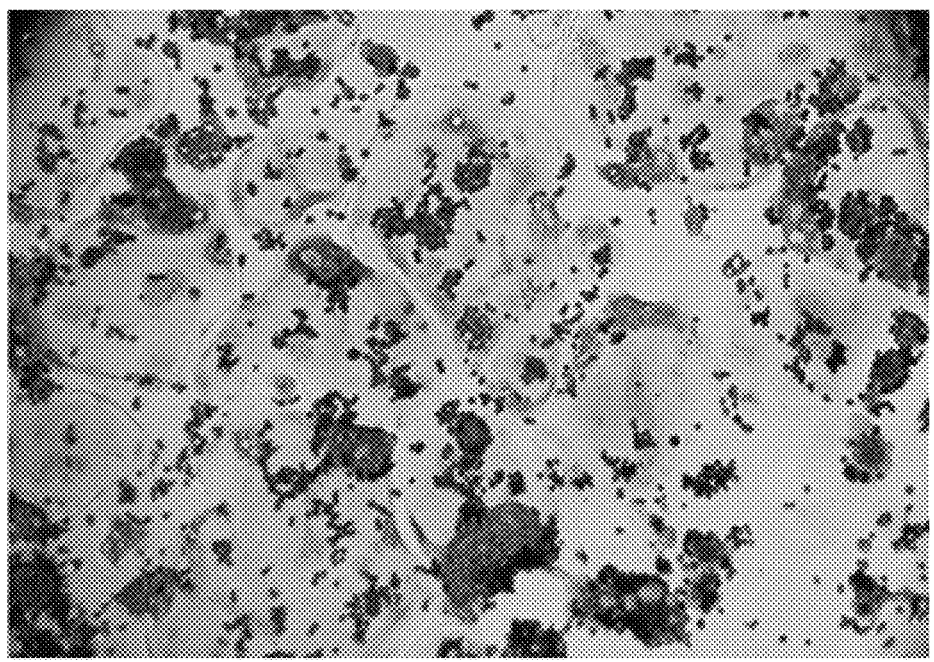
FIG. 2B shows the osteoclast differentiation of RAW264.7; RAW264.7 cells which were cultured without the compound 4 and compound 16 in the presence of RANKL.
Figure 2C:
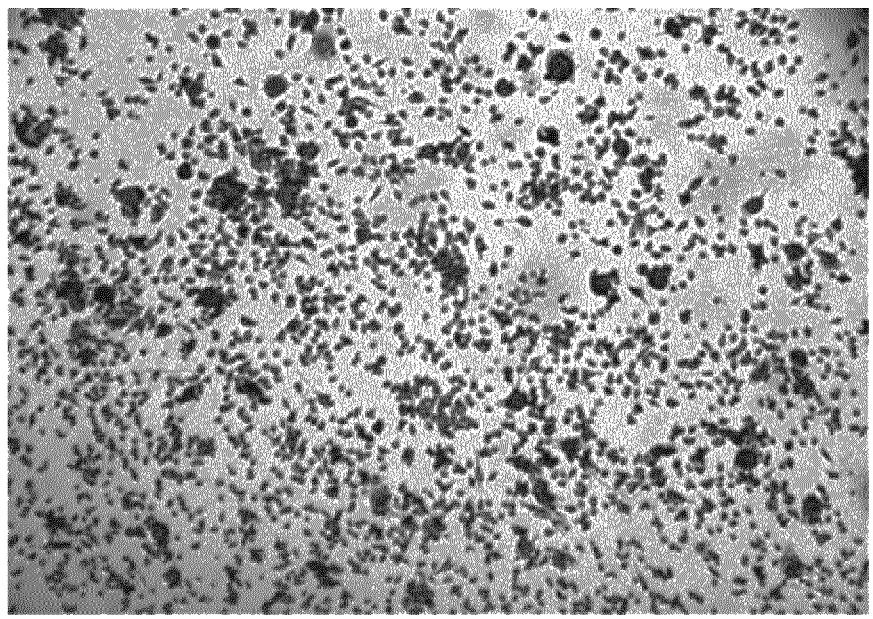
FIG. 2C shows the osteoclast differentiation of RAW264.7; RAW264.7 cells which were cultured with the compound 4 and compound 16 without the presence of RANKL.
Figure 2D:
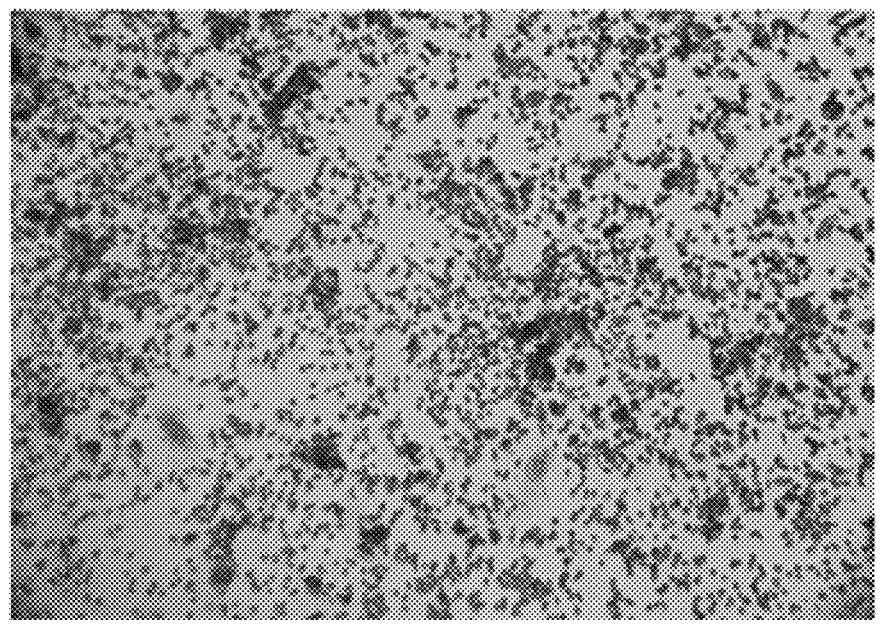
FIG. 2D shows the osteoclast differentiation of RAW264.7; RAW264.7 cells which were cultured with the compound 4 and compound 16 in the presence of RANKL.
Figure 3A:
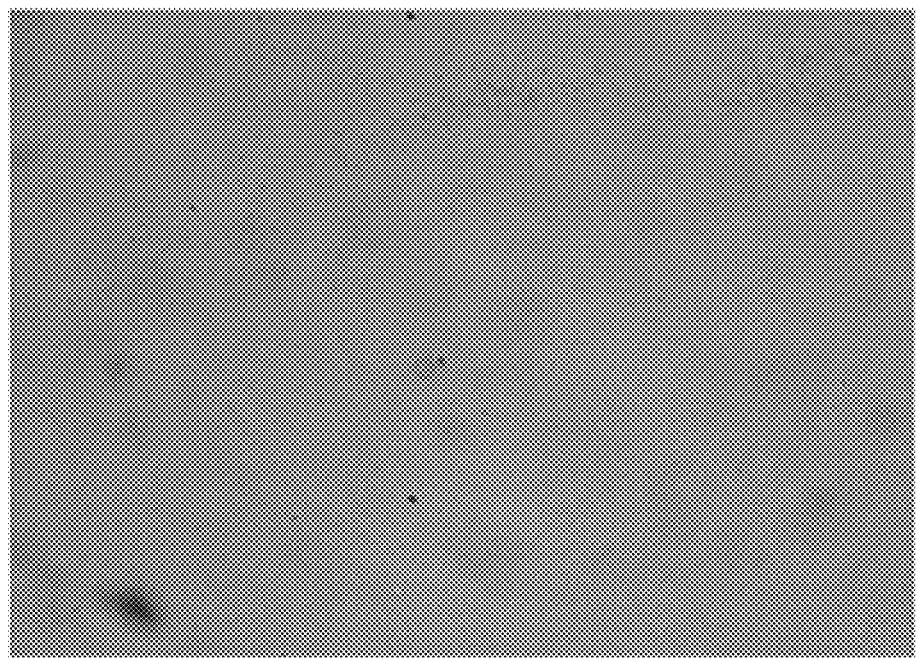
FIG. 3A is the Mayer's hematoxylin staining shows the effects of compound 4 and compound 16 on osteoclast differentiation of RAW264.7; RAW264.7 cells were cultured without compound 4 and compound 16 and without the presence of RANKL.
Figure 3B:
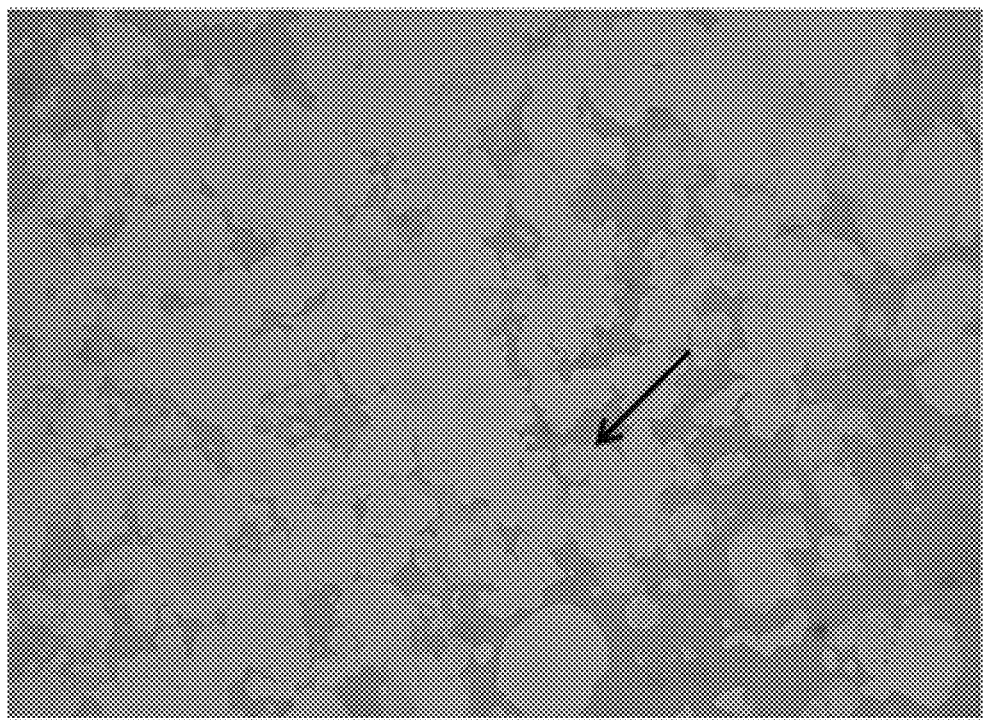
FIG. 3B is the Mayer's hematoxylin staining shows the effects of compound 4 and compound 16 on osteoclast differentiation of RAW264.7; RAW264.7 cells were cultured without compound 4 and compound 16 and in the presence of RANKL.
Figure 3C:
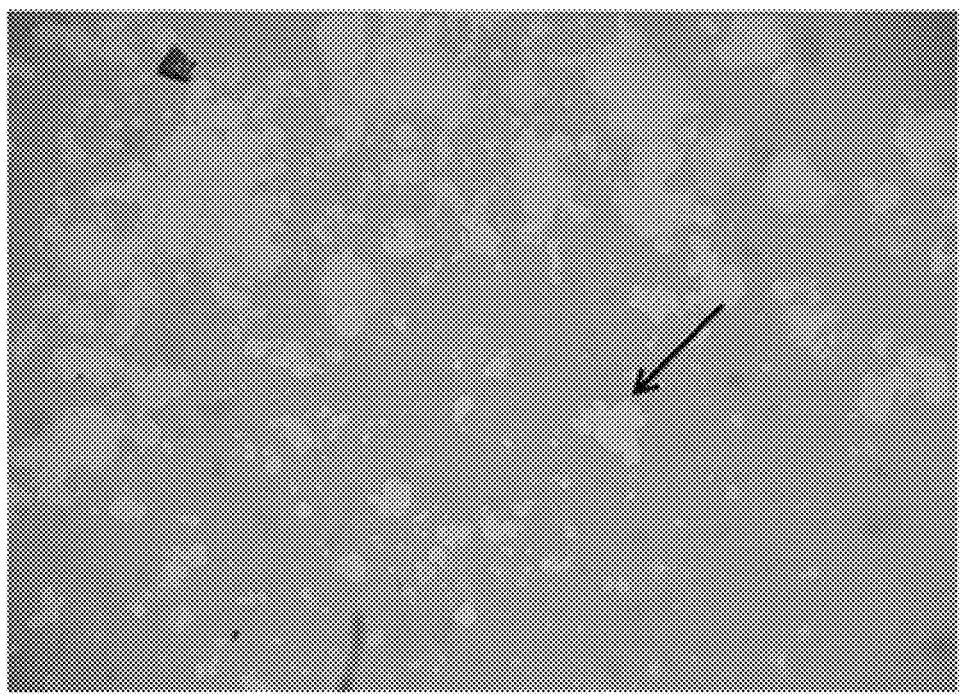
FIG. 3C is the Mayer's hematoxylin staining shows the effects of compound 4 and compound 16 on osteoclast differentiation of RAW264.7; RAW264.7 cells were treated with compound 4 and compound 16 and without the presence of RANKL.
Figure 3D:
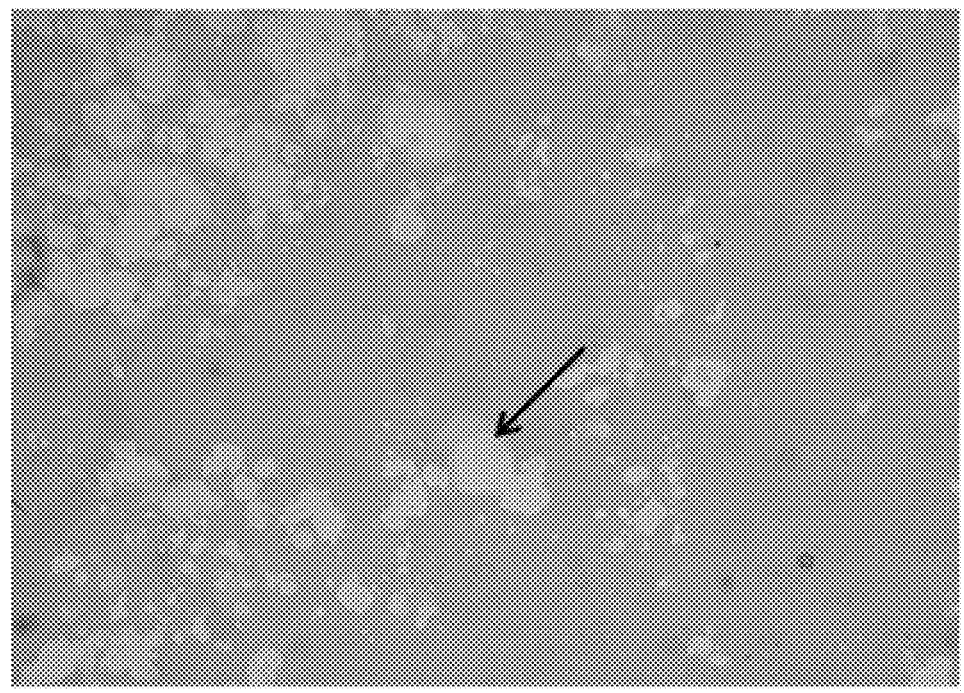
FIG. 3D is the Mayer's hematoxylin staining shows the effects of compound 4 and compound 16 on osteoclast differentiation of RAW264.7; RAW264.7 cells were treated with compound 4 and compound 16 and in the presence of RANKL.

By using pit formation assay, compounds 4 and 16 have effect on inhibition of resorption of osteoclast. RAW264.7 cells were cultured without compounds (compound 4 or compound 16, 5 µM) or treated with compounds (compound 4 or compound 16, 5 µM) in 24 well dentine slices plates in the presence of RANKL after 4 days, to identify the ability of resorption of osteoclast by observing the resorption pits formation. As shown in FIG. 1B, compared to the cell cultured without drug in the presence of RNAKL, the resorbed area of the cell cultured in compound 4 or 16 was only 23.11±2.25% and 20.11±1.51% respectively. It was obvious that compound 4 or 16 could inhibit the RANKL-induced resorption of osteoclast (FIG. 3A to D).

TABLE 3

Cell viability and $CC_{50}$ values of synthesized compounds in RAW 264.7 cells

| | RAW 264.7 cells | |
| --- | --- | --- |
| Compound | Cell viability (%) | $CC_{50}$ |
| 1 | 77.54 ± 1.17 | 17.85 |
| 2 | 109.62 ± 3.37 | >20 |
| 3 | 78.42 ± 3.79 | 14.59 |
| 4 | 102.46 ± 1.10 | 14.56 |
| 5 | 99.37 ± 3.71 | >20 |
| 6 | 96.73 ± 1.18 | 14.35 |
| 7 | 85.22 ± 3.83 | 10.38 |
| 8 | 62.95 ± 0.85 | >20 |
| 9 | 72.15 ± 0.36 | 12.27 |
| 10 | 96.24 ± 2.29 | 14.39 |
| 11 | 98.87 ± 2.06 | >20 |
| 12 | 104.90 ± 2.62 | >20 |
| 13 | 96.22 ± 0.53 | >20 |
| 14 | 96.49 ± 1.86 | 12.73 |
| 15 | 72.15 ± 0.43 | 9.96 |
| 16 | 86.60 ± 5.69 | 10.81 |
| 17 | 95.53 ± 3.86 | 15.13 |
| 18 | 100.13 ± 0.94 | 12.98 |
| 19 | 103.01 ± 2.51 | 15.48 |
| 20 | 88.38 ± 4.65 | 11.01 |
| 21 | 102.79 ± 1.93 | 14.86 |
| 22 | 108.33 ± 1.10 | >20 |
| 23 | 103.05 ± 4.03 | >20 |
| 24 | 105.53 ± 4.7 | >20 |
| Diflunisal | 103.82 ± 1.78 | >20 |

TABLE 4

Effects of Inhibitory osteoclast differentiation by compounds 1 to 24 in RAW 264.7 cells

| Compound | RAW 264.7cell Inhibition of MNCs (%) |
| --- | --- |
| 1 | 44.30 ± 7.93 |
| 2 | 32.24 ± 5.58 |
| 3 | 47.37 ± 5.58 |
| 4 | 67.32 ± 4.38 |
| 5 | 42.76 ± 6.51 |
| 6 | 59.21 ± 2.28 |
| 7 | 51.54 ± 6.25 |
| 8 | 40.57 ± 2.01 |
| 9 | 71.32 ± 3.39 |
| 10 | 13.87 ± 1.23 |
| 11 | 51.93 ± 6.50 |
| 12 | 40.79 ± 2.65 |
| 13 | 19.41 ± 1.40 |
| 14 | 42.32 ± 6.62 |
| 15 | 17.35 ± 7.49 |
| 16 | 86.84 ± 1.74 |
| 17 | 31.58 ± 4.00 |
| 18 | 62.92 ± 2.65 |
| 19 | 16.85 ± 4.61 |
| 20 | 57.46 ± 3.25 |
| 21 | 33.99 ± 6.98 |
| 22 | 29.44 ± 5.48 |
| 23 | 21.20 ± 2.49 |
| 24 | 30.75 ± 5.77 |
| Diflunisal | 23.91 ± 1.88 |

EXAMPLE 27

The Anti-Inflammatory Pharmaceutical Application of Compounds 1~24 in the Present Invention The synthesized 24 biphenyl benzamide-derived derivatives drug, compounds 1 to 24, can be used as anti-osteoporosis agent, also can be a potential anti-inflammatory agent. After modified, most of the compounds performed stronger anti-inflammatory effect than difunisal of original NSAID (Nonsteroidal anti-inflammatory drugs).

Isolation and Culture of Porcine Chondrocytes

Porcine cartilage was obtained from the hind leg joints of pigs. The synthesis of chondrocytes from cartilage was performed according to our previous report. After enzymatic digestion of articular cartilage with 2 mg/mL protease in serum-free Dulbecco's modified Eagle's medium (DMEM)/antibiotics, the specimens were then digested overnight with 2 mg/mL collagenase I and 0.9 mg/ml, hyaluronidase in DMEM containing 10% fetal bovine serum (FBS). The cells were collected, passed through a cell strainer (Becton Dickinson, Mountain View, Calif., USA), and cultured in DMEM containing 10% PBS and antibiotics for 3-4 days before use.

Cytotoxicity Assay by Lactate Dehydrogenase (LDH) Leakage

The measurement of the concentrations of the released lactate dehydrogenase (LDH), as an indicator of damage to the plasma membrane, was performed according to the manufacturer's instructions (Roche, Indianapolis, Ind., USA). The percent cytotoxicity was calculated as ([sample value−medium control]/[high control−medium control])×100. Individual sample values were the averages of the absorbance values in treated culture supernatants after subtraction of the absorbance values in background control in triplicate. Similarly, the average absorbance values of untreated cell culture supernatants, used as the medium control, were calculated. Equal amount of cells treated with 1% Triton X-100 was taken as the high control.

Measurement of NO Concentrations

Figure 4:
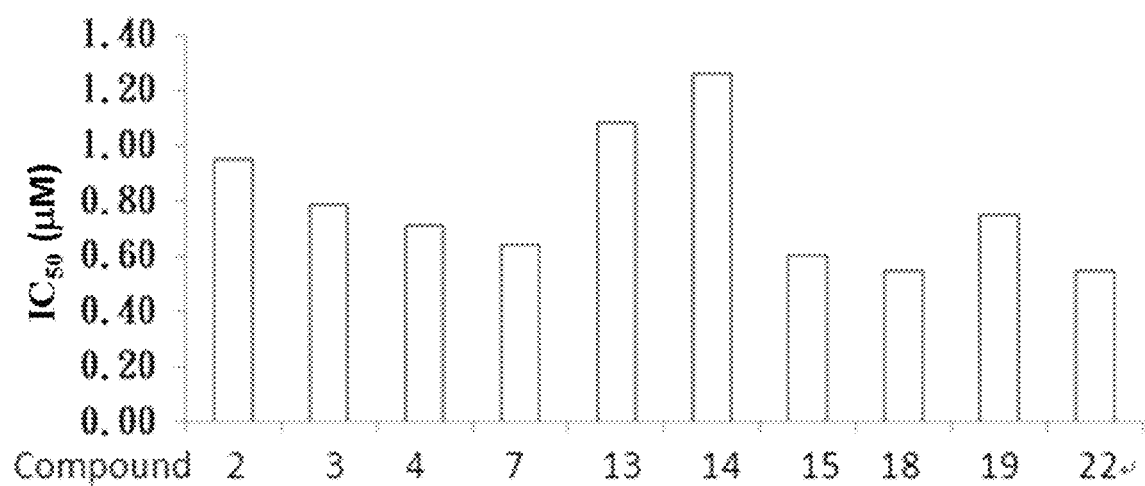
FIG. 4 shows the $IC_{50}$ value of the compounds of the present invention on anti-inflammatory reaction.

The measurement of NO release was reflected by determination of its stable end product, nitrite, in supernatants. The Griess reaction was performed with the concentrations of nitrite measured by a spectrophotometer. In brief, an aliquot (100 µL) of culture supernatant was incubated with 50 µL of 0.1% sulfanilamide in 5% phosphoric acid and 50 µL of 0.1% N-1-naphthyl-ethylenediamine dihydrochloride. After 10 min of incubation at room temperature, the absorbance was measured at 550 nm wavelength with a plate reader (recall, Grodig, Australia). The result was showed in Table 5 and FIG. 4. By viewing the $IC_{50}$ values of synthesized compounds on NO production, the compound 18 (IC50=0.55) performed best effect on inflammatory factor—NO inhibition.

TABLE 5

The anti-inflammatory $IC_{50}$ (μM) a value of compounds 1 to 24 in the present invention

| Compound | $IC_{50}$ (μM)$^a$ |
|---|---|
| compound 1 | 7.94 |
| compound 2 | 0.95 |
| compound 3 | 0.79 |
| compound 4 | 0.71 |
| compound 5 | >10 |
| compound 6 | 0.71 |
| compound 7 | 0.64 |
| compound 8 | 2.45 |
| compound 9 | >10 |
| compound 10 | >10 |
| compound 11 | 1.5 |
| compound 12 | 2.24 |
| compound 13 | 1.08 |
| compound 14 | 1.26 |
| compound 15 | 0.61 |
| compound 16 | 1.15 |
| compound 17 | >10 |
| compound 18 | 0.55 |
| compound 19 | 0.75 |
| compound 20 | 1.63 |
| compound 21 | >10 |
| compound 22 | 0.55 |
| compound 23 | 0.47 |
| compound 24 | 1.95 |
| Diflunisal | >10 |

As mentioned above, the present invention provides a series of pharmaceutical compositions of biphenyl benzamide-derived derivatives, the pharmaceutical acceptable salt and adjuvant, which perform effect on inhibition of osteoclast genesis, so as to prevent the osteoporosis effectively. In summary, the present invention provides biphenyl benzamide-derived derivatives with high salt-resistance and provides a method for increasing the salt resistance of antibacterial peptide to solve the problem that the salt-resistance of antibacterial peptide is low.

What is claimed is:

1. A biphenyl benzamide-derived derivatives, which structure is selected from formula I:

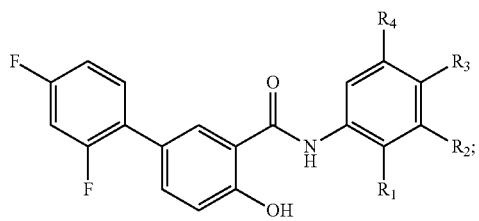

wherein said R1, R2, R3 and R4 of the formula I are selected from the group consisting of H, halogen, CN, CH and OCH3.

2. A pharmaceutical composition of biphenyl benzamide-derived derivatives, which comprises:

(a) a structure selected from formula I:

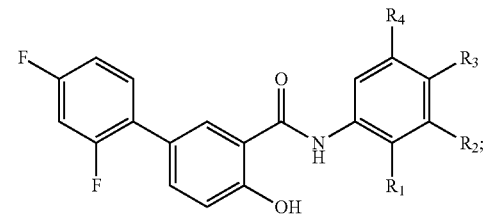

and (b) a pharmaceutical acceptable salt and carrier of the biphenyl benzamide-derived derivatives;

wherein said R1, R2, R3 and R4 of the formula I are selected from the group consisting of H, halogen, CN, CH and OCH3.

3. The pharmaceutical composition of claim 2, wherein the pharmaceutical acceptable carrier is an excipient, diluents, thickeners, filler, binder, disintegrants, lubricant, oil or non-oil base, surfactant, suspending agent, gelling agent, adjuvant, anti-corrosive agent, anti-oxidant, stabilizer, coloring agent or flavor.

4. The pharmaceutical composition of claim 2, wherein the salt is a physiologically acceptable salt of an inorganic acid, inorganic base, organic acid or organic base.

5. The pharmaceutical composition of claim 2, wherein said composition is a powder, granule, liquid, gel or cream.

6. The pharmaceutical composition of claim 2 wherein said composition is administered through an oral, transdermal, injection, or inhalational manner.

7. A method for synthesis of benzamide-derived derivatives, wherein a compound of formula I is synthesized by difunisal:

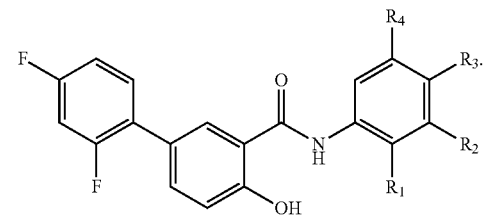

8. The method of claim 7, wherein the compound of formula I is synthesized by amine, tetrahydrofuran and an intermediate compound which is synthesized by difunisal, tetrahydrofuran and thionyl chloride.

9. A method of treating osteoporosis or osteoarthritis with an anti-inflammatory agent of biphenyl benzamide-derived derivatives comprising:

administering an effective amount of the anti-inflammatory agent of biphenyl benzamide-derived derivatives to a subject in need thereof, wherein the anti-inflammatory agent of biphenyl benzamide-derived derivatives comprises a structure of formula I:
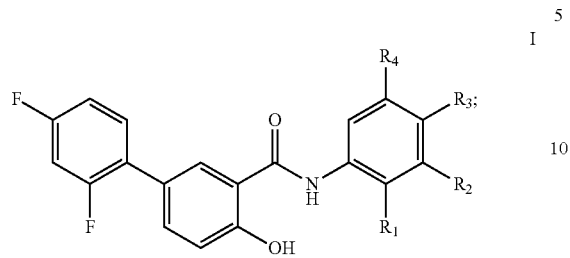
wherein said R1, R2, R3 and R4 of the formula II are selected from the group consisting of H, halogen, CN, CH3 and OCH3.
* * * * *